United States Patent
Kim et al.

(10) Patent No.: US 9,637,761 B2
(45) Date of Patent: May 2, 2017

(54) RECOMBINANT MICROORGANISM METABOLIZING 3,6-ANHYDRIDE-L-GALACTOSE AND A USE THEREOF

(71) Applicant: Korea University Research and Business Foundation, Seoul (KR)

(72) Inventors: Kyoung Heon Kim, Seoul (KR); In-Geol Choi, Seoul (KR); Eun-Ju Yun, Seoul (KR); Sae Young Lee, Gyeonggi-do (KR); Hee Taek Kim, Jeju-do (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 14/889,376

(22) PCT Filed: May 7, 2014

(86) PCT No.: PCT/KR2014/004033
§ 371 (c)(1),
(2) Date: Nov. 5, 2015

(87) PCT Pub. No.: WO2014/182054
PCT Pub. Date: Nov. 13, 2014

(65) Prior Publication Data
US 2016/0115504 A1    Apr. 28, 2016

(30) Foreign Application Priority Data

May 7, 2013 (KR) .................. 10-2013-0051134
Jun. 18, 2013 (KR) .................. 10-2013-0069750
May 7, 2014 (KR) .................. 10-2014-0054263

(51) Int. Cl.
C12P 7/06        (2006.01)
C12N 15/52       (2006.01)
C12N 9/02        (2006.01)
C12N 9/12        (2006.01)
C12N 9/88        (2006.01)
C12N 9/90        (2006.01)

(52) U.S. Cl.
CPC ............ *C12P 7/065* (2013.01); *C12N 9/0008* (2013.01); *C12N 9/12* (2013.01); *C12N 9/1205* (2013.01); *C12N 9/88* (2013.01); *C12N 9/90* (2013.01); *C12N 15/52* (2013.01); *C12Y 102/01* (2013.01); *C12Y 207/01058* (2013.01); *C12Y 401/02014* (2013.01); *C12Y 505/01* (2013.01); *C12Y 207/00* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 6,395,299 B1 | 5/2002 | Babich et al. | |
| 2011/0008861 A1 | 1/2011 | Berry et al. | |
| 2011/0312052 A1 | 12/2011 | Koltermann et al. | |
| 2012/0149092 A1 | 6/2012 | Green et al. | |

FOREIGN PATENT DOCUMENTS

| | | |
|---|---|---|
| KR | 2012-0085364 A | 8/2012 |
| WO | 2012102552 A2 | 8/2012 |

OTHER PUBLICATIONS

Ochman et al., "Genetic Applications of an Inverse Polymerase Chain Reaction," Genetics (Nov. 1988); 120:621-623.
Yun et al., "Production of 3,6-anhydro-L-galactose from agarose by agarolytic enzymes of Saccharophagus degradans 2-40," Process Biochemistry (2011); 46:88-93.
Yun et al., "Enzymatic production of 3,6-anhydro-l-galactose from agarose and its purification and in vitro skin whitening and anti-inflammatory activities," Appl Microbiol Biotechnol (2013); 97:2961-2970.
Roh et al., "Genome Sequence of *Vibrio* sp. Strain EJY3, an Agarolytic Marine Bacterium Metabolizing 3,6-Anhydro-L-Galactose as a Sole Carbon Source," Journal of Bacteriology (Apr. 24, 2012); vol. 194(10)2773-2774.
Yun et al., "The novel catabolic pathway of 3,6-anhydro-L-galactose, the main component of red macroalgae in a marine bacterium," Evironmental Microbiology (2015); 17(5):1677-1688.
Wei et al., "Marine macroalgae: an untapped resource for producing fuels and chemicals," Trends in Biotechnology (Feb. 2013); 31(2):70-77.
Databe UniProt Online XP002764525 (Apr. 18, 2006)—1 page, Accession No. Q21HC1.
Database UniProt Online XP002764526 (Jul. 25, 2006)—1 page, Accesion No. Q15SS2.

*Primary Examiner* — Rebecca Prouty
(74) *Attorney, Agent, or Firm* — Fox Rothschild LLP

(57) ABSTRACT

The present invention relates to a recombinant microorganism metabolizing 3,6-anhydro-L-galactose and a use thereof, and, more particularly, can produce ethanol from a recombinant microorganism expressing an enzyme group involved in a metabolic pathway of 3,6-AHG.

9 Claims, 11 Drawing Sheets

RECOMBINANT MICROORGANISM METABOLIZING 3,6-ANHYDRIDE-L-GALACTOSE AND A USE THEREOF

CROSS-REFERENCE TO RELATED APPLICATIONS

This application is the U.S. National Phase of International Application No. PCT/KR2014/004033, filed May 7, 2014, which claims priority to Korean Application Nos. 10-2013-0051134, filed May 7, 2013, 10-2013-0069750, filed Jun. 18, 2013 and 10-2014-0054263, filed May 7, 2014, the disclosures of which are all incorporated herein by reference.

TECHNICAL FIELD

The present invention relates to a recombinant microorganism metabolizing a non-fermentable sugar such as 3,6-anhydro-L-galactose and a use thereof.

BACKGROUND ART

With an energy crisis due to the depletion of petroleum resources, efforts are being made to develop energy resources replacing fossil fuels all around the world. As a part of such efforts, research for developing biofuels and biochemical materials which can replace fossil fuels with biomass to turn into a sustainable carbon economy and change a conventional chemical process into an environmentally-friendly bioprocess. The bioprocess is a new industry sector that can shift paradigm for upstream & downstream industries, and reduce a green house gas and a waste product.

As biomass for producing biofuels, the first-generation sugar-based biomass such as corn and sugarcane was changed into the second-generation lignocellulosic biomass, and recently the third-generation algae-based biomass is in the spotlight.

Among the algae-based biomass, red algae such as *Gelidium amansii* is known to have a higher carbohydrate content than those of green and brown algae, and agarose, which is the main polysaccharide constituting the red algae, is a polymer of 3,6-anhydro-L-galactose and D-galactose. The D-galactose is a fermentable monosaccharide that can be easily used by a microorganism, and has been widely studied to produce bioethanol by fermenting the D-galactose produced with a microorganism by hydrolyzing red algae biomass by a chemical or enzymatic treatment. Recently, an enzyme converting 3,6-anhydro-L-galactose was identified from microorganisms degrading agarose such as *Saccharophagus degradans* 2-40 and *Pseudoalteromonas atlantica* T6c (PCT/KR2012/000607). In addition, since a genomic sequence of *Vibrio* sp. EJY3, which is a microorganism capable of metabolizing 3,6-anhydro-L-galactose, known as a non-fermentable rare sugar, as a carbon source, is identified, a 3,6-anhydro-L-galactose metabolism-associated gene of the strains and a function of the gene are also being identified.

Research on a method of producing 3,6-anhydro-L-galactose and its function (Yun E J, et al. *Process Biochem.* (2011) 46(1):88-93. Yun E J, et al. *Appl. Microbiol. Biotechnol.* (2013) 97(7): 2961-70) has been reported by the inventors. For example, a reducing end of the 3,6-anhydro-L-galactose is easily hydrated, and thus exhibits a moisturizing function. Also, it was identified that the 3,6-anhydro-L-galactose has skin whitening and antioxidizing functions, and also has an effect of preventing colon cancer (Yun E J, et al. *Appl. Microbiol. Biotechnol.* (2013) 97(7): 2961-70).

However, the 3,6-anhydro-L-galactose is known as a non-fermentable monosaccharide that cannot be generally used by a microorganism, and, even though about 60% of red algae biomass consists of carbohydrates, it serves as the main reason of a low yield of biofuels from the of red algae biomass.

DISCLOSURE

Technical Problem

The present invention is directed to providing a recombinant vector having enzyme family involved in a metabolic pathway of 3,6-anhydro-L-galactose, a recombinant microorganism transformed with the recombinant vector, and a method of producing ethanol from the recombinant microorganism.

Technical Solution

In one aspect, the present invention provides a recombinant vector for producing ethanol, which includes a gene encoding 3,6-anhydro-L-galactose dehydrogenase, a gene encoding 3,6-anhydrogalactonic acid cycloisomerase, a gene encoding 2-keto-3-deoxy-galactonic acid kinase, and a gene encoding 2-keto-3-deoxy-phosphogalactonic acid aldolase.

In another aspect, the present invention provides a recombinant microorganism for producing ethanol, which is transformed by a gene encoding 3,6-anhydro-L-galactose dehydrogenase, a gene encoding 3,6-anhydrogalactonic acid cycloisomerase, a gene encoding 2-keto-3-deoxy-galactonic acid kinase, and a gene encoding 2-keto-3-deoxy-phosphogalactonic acid aldolase.

In still another aspect, the present invention provides a method of producing ethanol, which includes fermenting the recombinant microorganism according to the present invention with one or more sugars selected from the group consisting of galactose and 3,6-anhydro-L-galactose as a carbon source.

In yet another aspect, the present invention provides a method of producing ethanol, which includes producing pyruvate by a reaction of a cell culture or cell extract of the recombinant microorganism according to the present invention with one or more substrates selected from the group consisting of galactose and 3,6-anhydro-L-galactose, and performing alcohol fermentation with the pyruvate.

Advantageous Effects

According to the present invention, a method of producing ethanol in a recombinant microorganism expressing enzyme family involved in a metabolic pathway of 3,6-anhydro-L-galactose can be provided.

Therefore, when a high value material is produced using red algae biomass, the method can be provided as the key technique that can increase a yield.

DESCRIPTION OF DRAWINGS

FIGS. 1A, 1B and 1C show gas chromatography-time of flight mass spectrometry (GC-TOF MS) analysis results for enzymatic reaction products of enzymes isolated and purified from recombinant microorganisms expressing 3,6-anhydro-L-galactose dehydrogenase or 3,6-anhydrogalactonic acid cycloisomerase according to the present invention, in which FIG. 1A is the peak of 3,6-anhydro-L-galactose, which is used as a substrate, FIG. 1B is the peak of 3,6-anhydrogalactonic acid, which is a reaction product of 3,6-anhydro-L-galactose dehydrogenase, and FIG. 1C is the peak of 2-keto-3-deoxy-galactonic acid, which is a reaction product of 3,6-anhydrogalactonic acid cycloisomerase.

FIGS. 2A and 2B show two dimensional nuclear magnetic resonance (NMR) analysis results for an enzymatic reaction product of 3,6-anhydro-L-galactose dehydrogenase isolated and purified from a recombinant microorganism expressing 3,6-anhydro-L-galactose dehydrogenase according to the present invention, in which FIG. 2A is the result of two dimensional heteronuclear single quantum coherence spectroscopy (HSQC) NMR analysis, and FIG. 2B is the result of two dimensional heteronuclear multiple bond correlation (HMBC) NMR analysis.

FIGS. 3A, 3B, 3C and 3D show the results of GC-TOF MS analysis and two dimensional NMR analysis for an enzymatic reaction product of 3,6-anhydrogalactonic acid cycloisomerase isolated and purified from a recombinant microorganism expressing the 3,6-anhydrogalactonic acid cycloisomerase according to the present invention, in which FIG. 3A is a mass spectrum analysis result obtained by GC-TOF MS with respect to 2-keto-3-deoxy-gluconic acid as a standard material, FIG. 3B is the one dimensional NMR analysis result for the enzymatic reaction product of the 3,6-anhydrogalactonic acid cycloisomerase, FIG. 3C is the result of two dimensional HMBC NMR analysis for the enzymatic reaction product of the 3,6-anhydrogalactonic acid cycloisomerase, and FIG. 3D is the result of two dimensional HMBC NMR analysis for the enzymatic reaction product of 3,6-anhydrogalactonic acid cycloisomerase.

MODES OF THE INVENTION

Figures 1A, 1B, 1C:
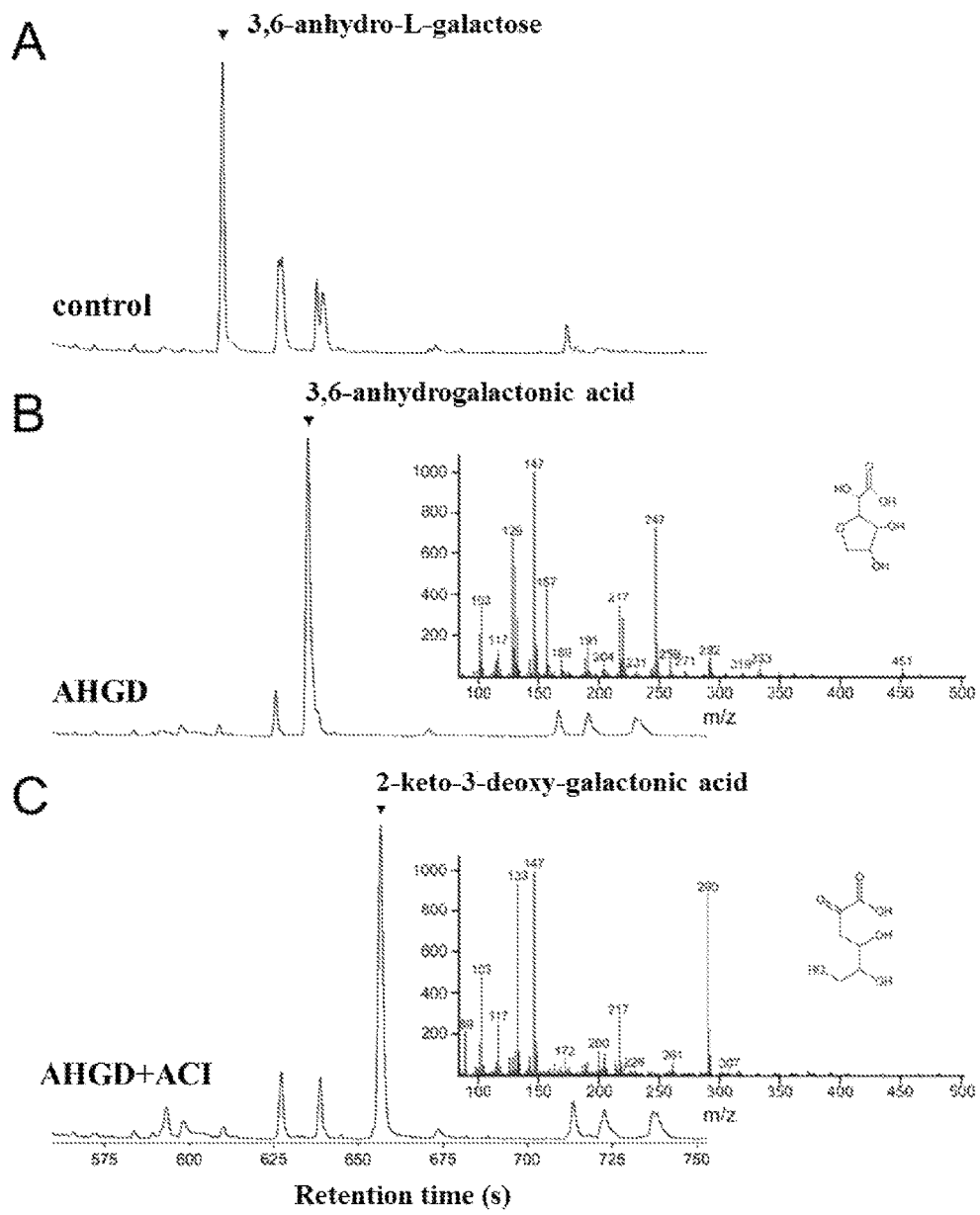

Hereinafter, the constitution of the present invention will be described in detail.

The present invention relates to a recombinant vector for producing ethanol, which includes a gene encoding 3,6-anhydro-L-galactose dehydrogenase, a gene encoding 3,6-anhydrogalactonic acid cycloisomerase, a gene encoding 2-keto-3-deoxy-galactonic acid kinase, and a gene encoding 2-keto-3-deoxy-phosphogalactonic acid aldolase.

The recombinant vector for producing ethanol of the present invention may produce ethanol as a final product using galactose and/or 3,6-anhydro-L-galactose (hereinafter, "3,6-AHG") as a substrate. More specifically, the recombinant vector includes a gene family encoding 3,6-anhydro-L-galactose dehydrogenase metabolizing 3,6-AHG, 3,6-anhydrogalactonic acid cycloisomerase responsible for the opening and isomerization of the ring structure of 3,6-anhydrogalactonic acid produced by the 3,6-anhydro-L-galactose dehydrogenase so as to convert to 2-keto-3-deoxy-galactonic acid, 2-keto-3-deoxy-galactonic acid kinase responsible for the phosphorylation of the 2-keto-3-deoxy-galactonic acid to 2-keto-3-deoxy-phosphogalactonic acid, and 2-keto-3-deoxy-phosphogalactonic acid aldolase responsible for the degradation of the 2-keto-3-deoxy-phosphogalactonic acid to pyruvate. The pyruvate is used as a starting material for alcohol fermentation, and ethanol is finally produced from the pyruvate through fermentation.

The 3,6-anhydro-L-galactose dehydrogenase is an enzyme responsible for the conversion of 3,6-AHG to 3,6-anhydrogalactonic acid and may originate from *Vibrio* sp. EJY3, *Saccharophagus degradans* 2-40 or *Pseudoalteromonas atlantica* T6c, and may be represented by, for example, a *Vibrio* sp. EJY3-derived base sequence set forth in SEQ ID NO: 1 and the amino acid sequence set forth in SEQ ID NO: 2.

The 3,6-anhydrogalactonic acid cycloisomerase is an enzyme responsible for the opening and isomerization of the ring structure of the 3,6-anhydrogalactonic acid so as to convert the 3,6-anhydrogalactonic acid to 2-keto-3-deoxy-galactonic acid and may originate from *Vibrio* sp. EJY3, *Saccharophagus degradans* 2-40 or *Pseudoalteromonas* atlantica T6c, and more specifically may be represented by any one of a *Saccharophagus degradans* 2-40-derived base sequence set forth in SEQ ID NO: 3 (the amino acid sequence: SEQ ID NO: 4), a *Pseudoalteromonas atlantica* T6c-derived base sequence set forth in SEQ ID NO: 5 (the amino acid sequence: SEQ ID NO: 6), and a *Vibrio* sp. EJY3-derived base sequence set forth in SEQ ID NO: 7 (the amino acid sequence: SEQ ID NO: 8).

The inventors first identified 3,6-anhydrogalactonic acid cycloisomerase producing linear 2-keto-3-deoxy-galactonic acid from 3,6-anhydrogalactonic acid (hereinafter, referred to as "AHGA") without a stoichiometric change as the result of an enzymatic reaction of proteins respectively obtained from genes forming a cluster with 3,6-anhydro-L-galactose dehydrogenase, which is one of the AHG metabolic enzymes, by genetic engineering techniques.

Therefore, the present invention also provides a composition for producing 2-keto-3-deoxy-galactonic acid, which includes 3,6-anhydrogalactonic acid cycloisomerase represented by any one of the amino acid sequences of SEQ ID NOs: 4, 6 and 8.

The present invention also provides 3,6-anhydrogalactonic acid cycloisomerase represented by any one of the amino acid sequences of SEQ ID NOs: 4, 6 and 8, a microorganism producing the 3,6-anhydrogalactonic acid cycloisomerase, or a method of producing 2-keto-3-deoxy-galactonic acid by a reaction of a culture of the microorganism with the AHGA.

The 2-keto-3-deoxy-galactonic acid kinase is an enzyme responsible for the phosphorylation of 2-keto-3-deoxy-galactonic acid to 2-keto-3-deoxy-phosphogalactonic acid and may originate from *Vibrio* sp. EJY3, *Saccharophagus degradans* 2-40 or *Pseudoalteromonas atlantica* T6c, and may be represented by the base sequence set forth in SEQ ID NO: 9 and the amino acid sequence set forth in SEQ ID NO: 10.

The 2-keto-3-deoxy-phosphogalactonic acid aldolase is an enzyme responsible for the degradation of 2-keto-3-deoxy-phosphogalactonic acid to pyruvate and may originate from *Vibrio* sp. EJY3, *Saccharophagus degradans* 2-40 or *Pseudoalteromonas atlantica* T6c, and may be represented by the base sequence set forth in SEQ ID NO: 11 and the amino acid sequence set forth in SEQ ID NO: 12.

The above-described genes include a polynucleotide encoding a protein which has a physiochemical activity of an enzyme and in which one or more amino acids are deleted, substituted, inserted and/or added. For example, the genes also include a polynucleotide having a nucleotide represented by any one of SEQ ID NOs: 1, 3, 5, 7, 9 and 11, and hybridized with the polynucleotide encoding the protein having the physiochemical property of the enzyme under severe conditions. The expression "polynucleotide hybridized under strict conditions" refers to a polynucleotide hybridized with one or more probe DNAs including a sequence of at least 20, and preferably at least 30 continuous residues (for example, 40, 60 or 100 continuous residues) arbitrarily selected from an enzyme protein, for example, under the conditions described in protocols (wash with primary washing buffer having 0.5×SSC at 42° C.) using an ECL direct nucleic acid labeling and detection system (Amersham Pharmacia Biotech). The polynucleotide of the present invention includes a isolated polynucleotide. The "isolated polynucleotide" refers to a polynucleotide existing in a different state from a naturally generated polynucleotide. For example, the isolated nucleotide includes a vector and a polynucleotide integrated into the genome of a different organism. Also, the isolated polynucleotide includes a polynucleotide obtained as cDNA, a PCR product, or a restriction fragment. Moreover, a polynucleotide used as a part of a polynucleotide encoding a fusion protein is included in the isolated polynucleotide.

The polynucleotides encoding the above-described enzymes of the present invention may be isolated, for example, by the following method: designing a PCR primer based on each of the nucleotide sequences of SEQ ID NOs: 1, 3, 5, 7, 9 and 11, and performing PCR using an enzyme-producing strain-derived chromosomal DNA or cDNA library as a template, and thereby DNA of the present invention is obtained.

Also, the polynucleotide of the present invention may be produced by screening (a) the library obtained by introducing a restriction fragment of the enzyme-producing strain-derived chromosomal DNA into a phage or plasmid and transforming *E. coli* cells with the phage or vector, or (b) the cDNA library through colony hybridization or plaque hybridization using a DNA fragment obtained as a probe.

Optionally, the polynucleotide of the present invention may be obtained by performing inverse PCR including analysis of a nucleotide sequence of the DNA fragment obtained by PCR, design of a PCR primer based on the sequence analyzed to elongate a strand in an external environment of a known DNA sequence, and digestion of the chromosomal DNA of the enzyme-producing strain with a suitable restriction enzyme and a self-cyclizing reaction using the DNA as a template (Genetics, (1988) 120: 621-623). The polynucleotide of the present invention may also be obtained by a rapid amplification of cDNA end (RACE) ("PCR Jikken Manual (Manual for PCR experiments)", 25-33, HBJ Publishing Bureau).

In addition to the genomic DNA and cDNA cloned by the above-described method, the polynucleotide of the present invention includes synthesized DNAs.

The term "recombinant vector" used herein is a vector which can express a target protein in suitable host cells, and refers to a gene construct having essential regulatory factors operably linked to express a gene insert. The vector may include, but is not limited to, a plasmid vector, a cosmid vector, a bacteriophage, or a virus vector. A suitable expression vector includes a signal sequence or leader sequence for membrane targeting or secretion as well as expression regulatory elements such as a promoter, an operator, a start codon, a termination codon, a polyadenylation signal, and an enhancer, and may be constructed in various forms depending on a purpose. The promoter of a vector may be constitutive or inducible. Also, the expression vector includes a selective marker for selecting host cells containing a vector, and if it is a replicable expression vector, includes the origin of replication.

The recombinant vector of the present invention is preferably constructed by inserting each or all of the above-described enzyme-coding nucleic acids into an expression vector for *E. coli* strains. The expression vector for *E. coli* strains may be any of the generally used expression vectors for *E. coli* strains without limitation.

The present invention also relates to a recombinant microorganism for producing ethanol transformed by a gene encoding 3,6-anhydro-L-galactose dehydrogenase, a gene encoding 3,6-anhydrogalactonic acid cycloisomerase, a gene encoding 2-keto-3-deoxy-galactonic acid kinase, and a gene encoding 2-keto-3-deoxy-phosphogalactonic acid aldolase.

The transformation includes any method for introducing a nucleic acid into an organism, cell, tissue or organ, and may be carried out by selecting suitable standard technique depending on host cells as known in the art. Such a method may be, but is not limited to, electroporation, protoplast fusion, calcium phosphate ($CaPO_4$) precipitation, calcium chloride ($CaCl_2$) precipitation, stirring with silicon carbide fibers, Agrobacterium-mediated transformation, PEG, dextrane sulfate, or lipofectamine.

Also, since an expression level and modification of a protein may vary depending on host cells, most suitable host cells may be selected depending on a purpose.

The host cells may be derived from, but are not limited to, a prokaryote such as *Escherichia coli, Bacillus subtilis, Streptomyces, Pseudomonas, Proteus mirabilis,* or *Staphy-* lococcus. The host cells may also be derived from a eukaryote such as a fungi (for example, Aspergillus) or a yeast (for example, *Pichia pastoris, Saccharomyces cerevisiae, Schizosaccharomyces*, and *Neurospora crassa*), but the present invention is not limited thereto. The transformant may be easily formed by introducing a recombinant vector having the genes into any host cells.

More specifically, the recombinant microorganism may be transformed with a recombinant vector having a gene encoding 3,6-anhydro-L-galactose dehydrogenase, a recombinant vector having a gene encoding 3,6-anhydrogalactonic acid cycloisomerase, a recombinant vector having a gene encoding 2-keto-3-deoxy-galactonic acid kinase, and a recombinant vector having a gene encoding 2-keto-3-deoxy-phosphogalactonic acid aldolase.

Alternatively, the recombinant microorganism may be transformed with a recombinant vector having a gene encoding 3,6-anhydro-L-galactose dehydrogenase and a gene encoding 3,6-anhydrogalactonic acid cycloisomerase, a recombinant vector having a gene encoding 2-keto-3-deoxy-galactonic acid kinase, and a recombinant vector having a gene encoding 2-keto-3-deoxy-phosphogalactonic acid aldolase.

Alternatively, the recombinant microorganism may be transformed with a recombinant vector having a gene encoding 3,6-anhydro-L-galactose dehydrogenase, a gene encoding 3,6-anhydrogalactonic acid cycloisomerase, a gene encoding 2-keto-3-deoxy-galactonic acid kinase, and a gene encoding 2-keto-3-deoxy-phosphogalactonic acid aldolase.

The recombinant microorganism according to the present invention may be a fermentation strain.

The present invention also relates to a method of producing ethanol, which includes fermenting the recombinant microorganism according to the present invention with one or more sugars selected from the group consisting of galactose and 3,6-AHG as a carbon source.

The recombinant microorganism according to the present invention may produce pyruvate, which is a starting material for alcohol fermentation, and thus produce ethanol using galactose and/or 3,6-AHG as a carbon source by enzymes capable of metabolizing the 3,6-AHG under fermentation conditions.

During the fermentation, as an induction material, arabinose may be used.

The present invention also relates to a method of producing ethanol, which includes producing pyruvate by a reaction of a cell culture or cell extract of the recombinant microorganism according to the present invention with one or more substrates selected from the group consisting of galactose and 3,6-AHG, and performing alcohol fermentation with the pyruvate.

The recombinant microorganism according to the present invention may express a enzyme family capable of metabolizing 3,6-AHG, and since the cell culture or cell extract of the recombinant microorganism has the enzyme family, when reacting with galactose and/or 3,6-AHG as a substrate, pyruvate may be produced. The pyruvate may be a starting material for the alcohol fermentation, and ethanol may be produced from the pyruvate under fermentation conditions.

Hereinafter, the present invention will be described in detail. The following examples merely demonstrate the present invention, but the scope of the present invention is not limited to the following examples.

EXAMPLE 1

Production of Recombinant Microorganism for Expressing 3,6-anhydro-L-galactose dehydrogenase

*Vibrio* sp. EJY3-derived 3,6-anhydro-L-galactose dehydrogenase was cloned. To this end, the following set of primers were prepared based on information of the base sequence of a 3,6-anhydro-L-galactose dehydrogenase-encoding gene (ORF Names: VEJY3_09240).

```
Forward primer 1:
                                    (SEQ ID NO: 13)
5'-gaaggagatataaggatgaaacgttaccaaatgtacgttg-3'

Reverse primer 2:
                                    (SEQ ID NO: 14)
5'-atgatggtgatggtggtcgaaattcacatagaatgtcttc-3'
```

Each enzyme gene amplified by a PCR was cloned in a modified pET2 1 α(hereinafter, referred to as "pJL") vector to which six histidine residues were added to a pBAD vector (Invitrogen, Product no. V440-01) and an N-terminus, and used to transform an expression *E. coli* BL21 (DB3) to express the enzyme. PCR conditions used herein were as follows: 1) the initial denaturation: 97° C., 30 sec, 2) the annealing: 35 cycles: 97° C., 10 sec-57° C., 1 min-72° C., 2 min, and 3) the final extension: 72° C., 5 min.

3,6-anhydro-L-galactose dehydrogenase cloned in the pBAD vector induced expression using 0.2% (w/v) arabinose as an inducer at 16° C. and 200 rpm for 18 hours. The enzyme overexpressed in *E. coli* BL21 was purified using a His-trap column.

200 μg of the purified 3,6-anhydro-L-galactose dehydrogenase reacted with 10 mM 3,6-AHG and a 1.5 mM NADP cofactor in 20 mM Tris-HCl (pH 7.4) at 30° C. for 1 hour, a reaction product was analyzed by gas chromatography-time of flight mass spectrometry (GC-TOF MS), and a chemical structure was identified by two dimensional (2D) nuclear magnetic resonance (NMR).

A derivatization reaction was carried out on an enzymatic reaction product dried for the GC-TOF MS analysis. 5 μl of the resultant derivative was added to a solution prepared by dissolving 40 mg/mL of methoxyamine hydrochloride in pyridine (Sigma-Aldrich, St. Louis, Mo.) and allowed to react at 30° C. for 90 minutes. Afterward, 45 μl of N-methyl-N-trimethylsilyltrifluoroacetamide (Fluka, Buchs, Switzerland) was added and allowed to react at 37° C. for 30 minutes. The derivatized sample was analyzed using an Agilent 7890 A GC (Agilent Technologies, Wilmington, DE) coupled to a Pegasus HT TOF MS (LECO, St. Joseph, Mich.). An RTX-5Sil MS column (30 m×0.25 mm, 0.25-μm film thickness; Restek, Bellefonte, Pa.) was used, and 1 μl of the sample was injected in a splitless mode. An oven temperature was first 50° C., and a retention time was given for 1 minute, and the temperature was elevated to 330° C. at a rate of 20° C/min, and then a retention time given for 5 minutes. An ion source temperature was 250° C., and a temperature of a transfer line was 280° C. A scanning range of mass spectra was 85 to 500 m/z.

A reaction product was purified using a Sephadex G-10 column. That is, a chemical structure was identified with 2 mg of each of the purified reaction products using a Bruker Avance II 900 MHz NMR spectrometer through $^{13}$C NMR, $^1$H-$^{13}$C HSQC NMR and $^1$H-$^{13}$C HMBC NMR analyses. Here, an internal standard was 3-(trimethylsylyl)-propionic-2,2,3,3-d$_4$acid.

FIG. 1A shows 3,6-AHG used as a substrate, and FIG. 1B is the result of an enzymatic reaction with 3,6-anhydro-L-galactose dehydrogenase, which shows that AHGA was produced as a reaction product.

Figure 2A:
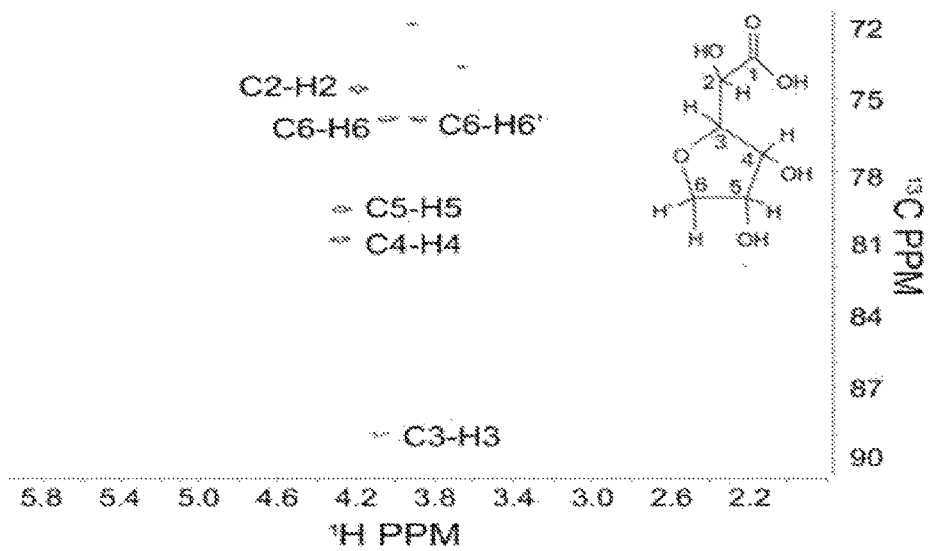
Figure 2B:
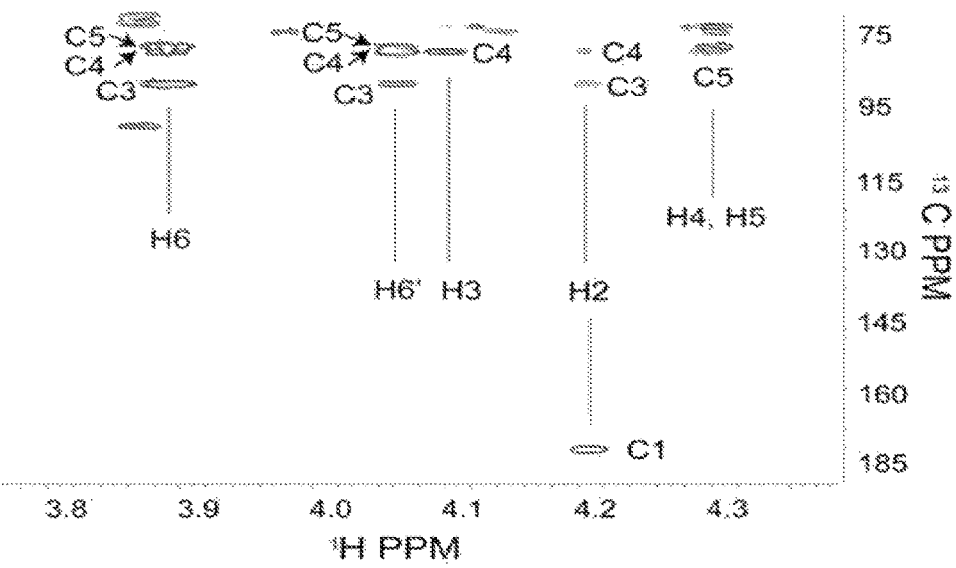

FIG. 2 is an NMR analysis result for a reaction product of the 3,6-anhydro-L-galactose dehydrogenase, which shows that, since a correlation spot between the first carbon and the first hydrogen was not found, an aldehyde group of the 3,6-AHG was converted by the enzymatic reaction of the 3,6-anhydro-L-galactose dehydrogenase (FIG. 2A), since correlation between the third carbon and the sixth hydrogen was found, a 3,6-anhydro bond was maintained as it was, and the spot of the first carbon was observed at about 180 PPM, the aldehyde group of the 3,6-AHG was oxidized to a carboxyl group (FIG. 2B).

Therefore, it was identified that the enzymatic reaction product of the 3,6-anhydro-L-galactose dehydrogenase was AHGA.

EXAMPLE 2

Production of Recombinant Microorganism for Expressing 3,6-anhydrogalactonic Acid cycloisomerase

*Saccharophagus degradans* 2-40, *Pseudoalteromonas atlantica* T6c, and *Vibrio* EJY3-derived 3,6-anhydro-L-galactose dehydrogenase were cloned. To this end, based on the information on ACI gene sequences (European Molecular Biology Laboratory (EMBL) base sequence database accession nos.: CP000282, 1152nt, CP000388, 1137nt and CP003241, 1089nt) obtained from genomic sequences of *Saccharophagus degradans* 2-40, *Pseudoalteromonas atlantica* T6c and *Vibrio* EJY3, the following set of primers was prepared.

```
1) Sde
Forward primer 1:
                            (47mer: SEQ ID NO: 15)
5'-gaaggagatataaggatgaaaattcataacatgaaaaatttat
caa-3'

Reverse primer 2:
                            (40mer: SEQ ID NO: 16)
5'-atgatggtgatggtgtcattcagcaaaatacactgtcttc-3'

2) Patl
Forward primer 1:
                            (43mer: SEQ ID NO: 17)
5'-gaaggagatataaggatgatgagtgtcattaccaaactagaca-3'

Reverse primer 2:
                            (42mer: SEQ ID NO: 18)
5'-atgatggtgatggtgagaatgtttaactaaatagggaagaag-3'

3) Vejy3
Forward primer 1:
                            (43mer: SEQ ID NO: 19)
5'-gaaggagatataaggatgaaaacaacaatcaaagacatcaaaa-3'

Reverse primer 2:
                            (38mer: SEQ ID NO: 20)
5'-atgatggtgatggtgcacttcgtactgagcaattttgt-3'
```

Each gene was amplified by PCR using corresponding genomic DNA as a template. To purify all N-terminal parts of the amplified sdeACI, patlACI, and vejy3ACI DNAs, they were cloned in a modified pET2 1 a (hereinafter, pJL) vector including a gene sequence encoding six histidine residues by ligation independent cloning (LIC), and transformed into an expression *E. coli* BL21 (DE3) strain. Conditions for the PCR used herein are as follows: 1) initial denaturation: 97° C., 30 sec, 2) annealing condition: 35 cycles: 97° C., 10 sec-57° C., 1 min-72° C., 2 min, and 3) final extension: 72° C., 5 min.

*E. coli* prepared by transforming E. coli BL21 (DE3) with a recombinant plasmid including each of the sdeACI, pat-lACI, and vejy3ACI genes was inoculated into a Luria-bertani medium containing 50 mg/L of ampicillin, and cultured by shaking at 37° C. until OD$_{600}$ approached 0.5 to 1.0. Afterward, expression was induced with 0.5 mM/L of isopropyl-β-D-thiogalactopranoside (IPTG) at 16° C. for 24 hours. A cell culture was centrifuged at 4000 rpm for 15 minutes, and a cell pellet suspended in 20 mM Tris-HCl buffer (pH 8.0) was disrupted using an ultrasonicator, thereby producing a crude extract. The crude extract was centrifuged at 4° C. and 15000 rpm for 40 to 60 minutes to separate a crude enzyme extract and a precipitate. After the crude enzyme extract was filtered with a 0.45 μm filter, a protein was purified by affinity chromatography, ion exchange chromatography, and gel filtration chromatography, in that order.

As the result of 10% SDS-PAGE analysis, an enzyme having a size of about 42 kDa may be obtained (not shown).

25 μg of the purified 3,6-anhydrogalactonic acid cycloisomerase (vejy3ACI) reacted with the reaction product obtained in Example 1 at 30° C. for 1 hour. The reaction product was analyzed by GC-TOF MS, and analyzed by two dimensional (2D) NMR analysis to identify a chemical structure thereof, and purified using a Sephadex G-10 column. The anaylses and purification methods are the same as described in Example 1. As a standard material, 2-keto-3-deoxy-gluconic acid (Sigma, Product no. 12271) was used.

As shown in FIG. 1C, it was confirmed that the reaction product was 2-keto-3-deoxy-galactonic acid.

Figure 3A:
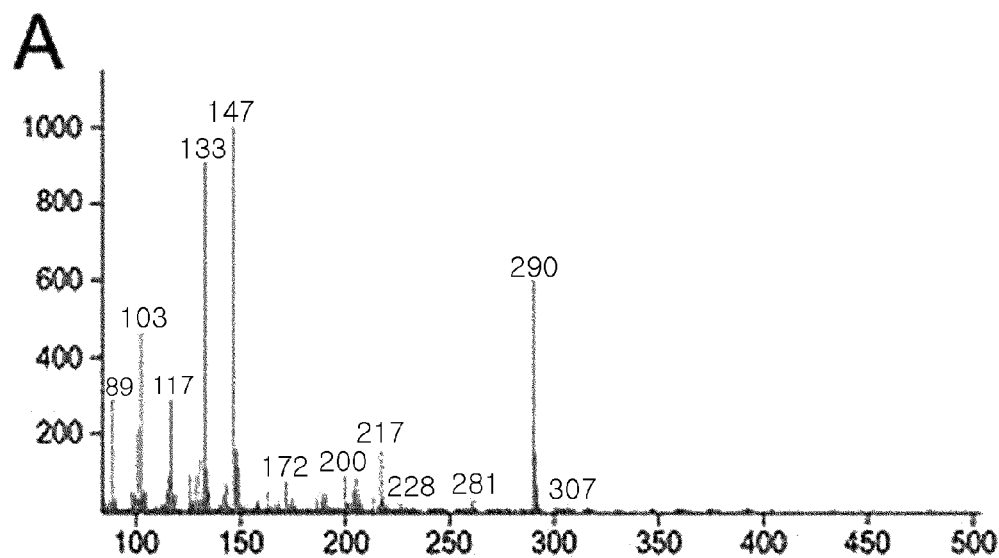
Figure 3B:
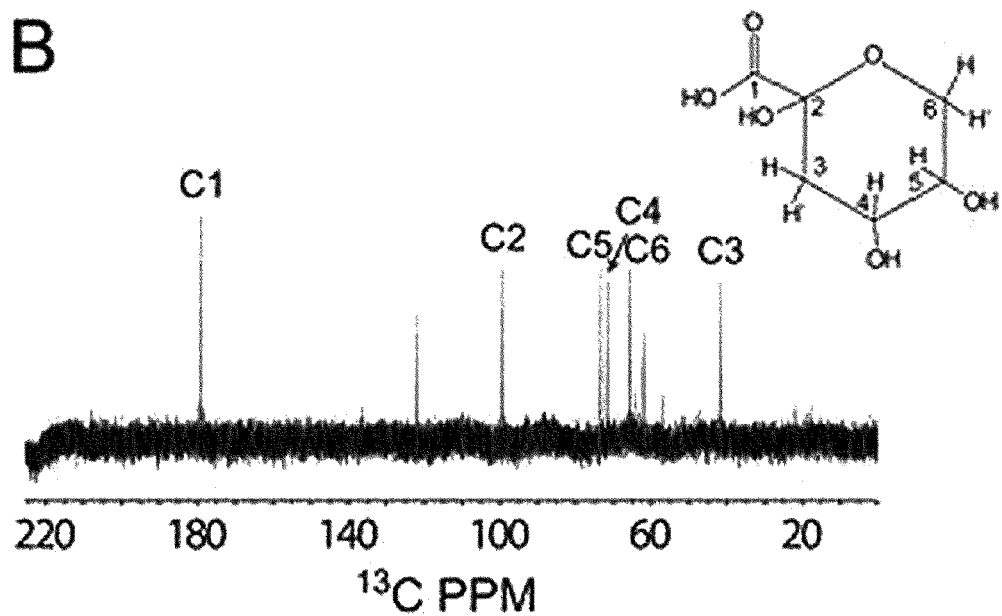
Figure 3C:
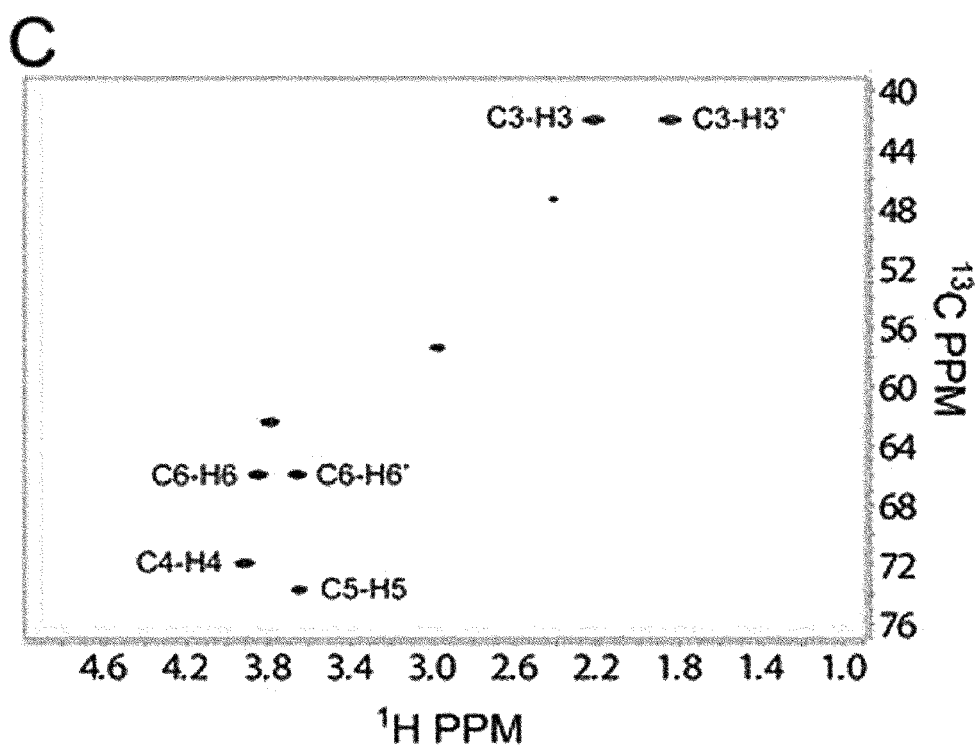
Figure 3D:
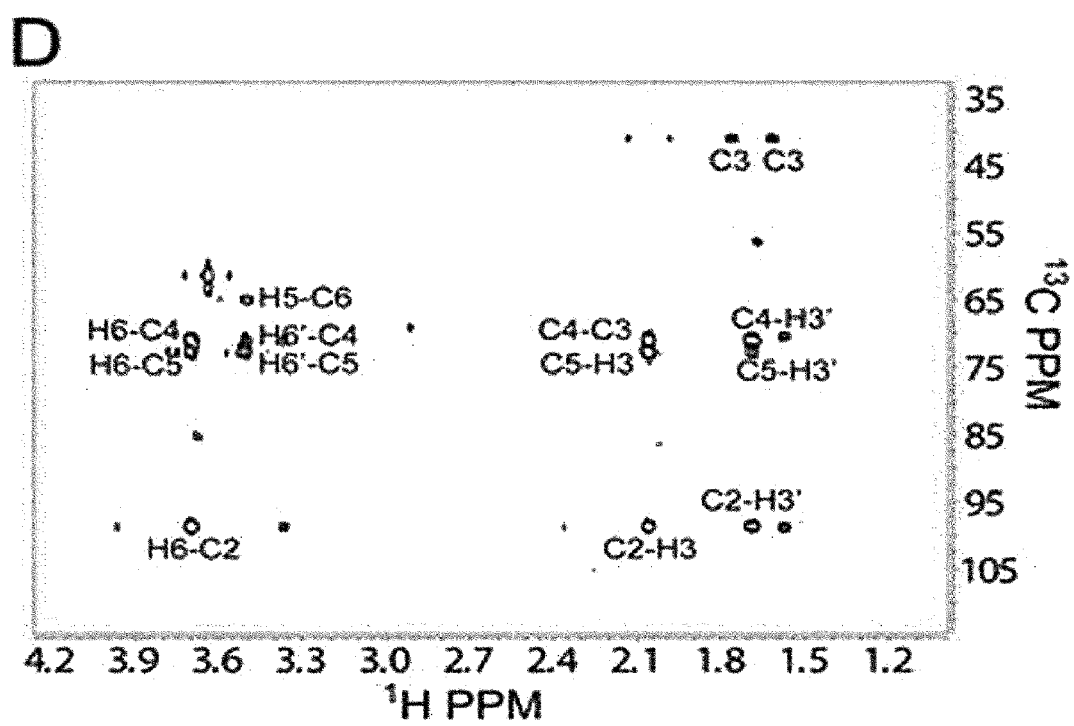

FIG. 3 shows NMR analysis results for a reaction product of 3,6-anhydrogalactonic acid cycloisomerase (vejy3ACI), in which, since the mass spectrum of a standard material such as 2-keto-3-deoxy-gluconic acid corresponded to that of an enzymatic reaction product of the 3,6-anhydrogalactonic acid cycloisomerase of FIG. 1C, it can be seen that the enzymatic reaction product of 3,6-anhydrogalactonic acid cycloisomerase is identified as a material having the same molecular weight and two dimensional (2D) structure of the 2-keto-3-deoxy-gluconic acid (FIG. 3A). Also, since peaks of a carboxyl group at the first carbon and a hemi-ketal structure at the second carbon are observed (FIG. 3B) and a correlation spot between the first carbon and the sixth hydrogen is not observed, it can be seen that the carboxyl group at the first carbon still exist (FIG. 3C). Also, since there is no correlation spot between the third carbon and the sixth carbon, it can be seen that the 3,6-anhydro bond is open, and since there is a correlation spot between the second carbon and the sixth hydrogen (FIG. 3D), and a carboxylic acid ($^{13}$C 180 PPM) signal still remains at the AHGA, it can be seen that the carboxylic acid at the first carbon still remains, and therefore the enzymatic reaction product of the 3,6-anhydrogalactonic acid cycloisomerase is identified as 2-keto-3-deoxy-galactonic acid.

EXAMPLE 3

Production of Recombinant Microorganism for Expressing 3,6-anhydro-L-galactose dehydrogenase and 3,6-anhydrogalactonic Acid cycloisomerase For the growth experiment for recombinant *E. coli*, genes encoding enzymes such as *Vibrio* sp. EJY3-derived 3,6- anhydro-L-galactose dehydrogenase, and 3,6-anhydrogalactonic acid cycloisomerase were individually or simultaneously cloned into a pBAD vector, and transformed into *E. coli* K12 MG1655. Information on primers used herein is as follows:

1. When the Enzyme-Encoding Genes were Individually Cloned 1.1. 3,6-anhydro-L-galactose dehydrogenase-encoding gene (ORF Names: VEJY3_09240)

```
Forward primer 1:
                                     (SEQ ID NO: 13)
5'-gaaggagatataaggatgaaacgttaccaaatgtacgttg-3'

Reverse primer 2:
                                     (SEQ ID NO: 14)
5'-atgatggtgatggtggtcgaaattcacatagaatgtcttc-3'
```

1.2. 3,6-anhydrogalactonic Acid cycloisomerase-Encoding gene (ORF Names: VEJY3_09370)

```
Forward primer 1:
(Tm: 61.9, XhoI)
                                     (SEQ ID NO: 21)
5'-gcgctcgagatgaaaacaacaatcaaagacatcaaaac-3'

Reverse primer 2:
(Tm: 61.8, SnabI)
                                     (SEQ ID NO: 22)
5'-gcgtacgtacacttcgtactgagcaattttgtc-3'
```

2. When the Enzyme-Encoding Genes were Simultaneously Cloned: 3,6-anhydro-L-galactose dehydrogenase-Encoding Gene (ORF Names: VEJY3_09240) and 3,6-anhydrogalactonic acid cycloisomerase-Encoding Gene (ORF Names: VEJY3_09370)

2.1. 3,6-anhydro-L-galactose dehydrogenase-Encoding Gene (VEJY_3_09240)

```
Forward primer 1:
(XhoI)
                                     (SEQ ID NO: 23)
5'-gcgctcgagatgaaacgttaccaaatgtacgttg-3'

Reverse primer 2:
(XbaI)
                                     (SEQ ID NO: 24)
5'-gcgtctagattagtcgaaattcacatagaatgtct-3'
```

2.2. 3,6-anhydrogalactonic Acid cycloisomerase-Encoding Gene (VEJY3_09370)

```
Forward primer 1:
(XbaI)
                                     (SEQ ID NO: 21)
5'-gcgtctagaatgaaaacaacaatcaaagacatcaaaac-3'

Reverse primer 2:
(SnabI)
                                     (SEQ ID NO: 22)
5'-gcgtacgtacacttcgtactgagcaattttgtc-3'
```

When the 3,6-anhydro-L-galactose dehydrogenase-encoding gene (ORF Names: VEJY3_09240) and the 3,6-anhydrogalactonic acid cycloisomerase-encoding gene (ORF Names: VEJY3_09370) were simultaneously cloned into pBAD, an XbaI restriction site of the VEJY3_09240 primer 2 was designed to be joined with an XbaI restriction site of the VEJY3_09370 primer 1 by ligation, and XhoI and SnabI restriction sites at the ends of the VEJY3_09240 and VEJY3_09370, which were joined to each other, were designed to be joined with the pBAD vector.

Each enzyme produced by cloning the enzyme-encoding gene into the pBAD vector and transforming *E. coli* K12 MG1655 with the vector was expressed with 0.01% (w/v) arabinose. The *E. coli* K12 MG1655 strain having each enzyme-encoding gene was cultured in a modified M9 medium. A method of preparing the M9 medium is as follows. In order to prepare a 5-fold concentrated M9 salt solution, 2.5 g of NaCl, 5 g of NH$_4$Cl and 250 mM of a Tris-HCl buffer (pH 7.4) were dissolved in 1L water and sterilized. 2 mL of 1M MgSO$_4$, 0.1 mL of 1M CaCl$_2$, 20 mL of 20% (w/v) 3,6-AHG, and 20 mL of a 5% (w/v) yeast nitrogen base (YNB) were added to 200 mL of the 5-fold concentrated M9 salt solution, and distilled water was added to a total volume of 1L. Culture conditions for the recombinant *E. coli* K12 MG1655 were 30° C. and 200 rpm.

Figure 4:
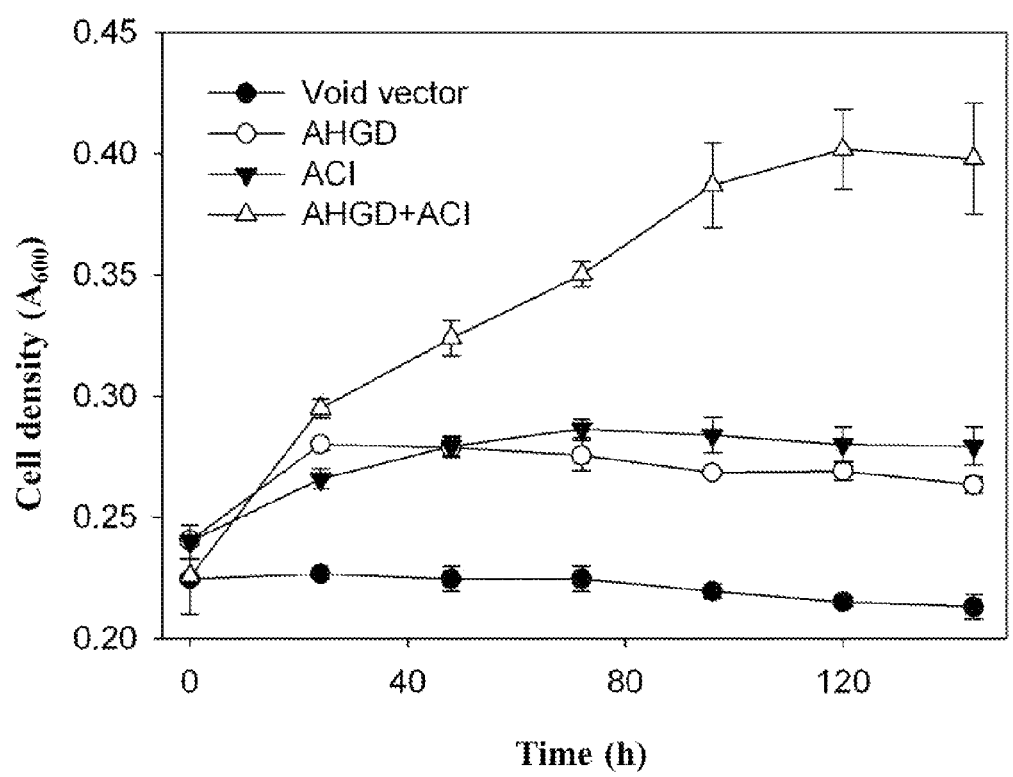
FIG. 4 shows a growth curve experiment result for recombinant microorganisms individually or simultaneously expressing 3,6-anhydro-L-galactose dehydrogenase and 3,6-anhydrogalactonic acid cycloisomerase according to the present invention using 3,6-anhydro-L-galactose as a carbon source.

As the result of culturing the recombinant microorganism using 1% (w/v) 3,6-AHG as a carbon source and 0.01%(w/v) arabinose, as shown in FIG. 4, the recombinant *E. coli* K12 MG1655 was not grown at all under the condition of an empty vector without a gene, and the recombinant *E. coli* expressing the enzymes such as the 3,6-anhydro-L-galactose dehydrogenase and the 3,6-anhydrogalactonic acid cycloisomerase was grown a little, and the recombinant *E. coli* simultaneously expressing the 3,6-anhydro-L-galactose dehydrogenase and the 3,6-anhydrogalactonic acid cycloisomerase showed the highest growth.

The recombinant microorganism was cultured in an M9 medium under an aerobic condition at 30° C. for 96 hours, and the absorbance was measured at 600 nm. Here, as a carbon source, an agarose hydrolysate predominantly containing 20 mL of 20% (w/v) 3,6-AHG, 3,6-AHG and galactose was used. Here, as a carbon source, an agarose hydrolysate predominantly containing 3,6-AHG, 3,6-AHG and galactose was used.

Figures 5A, 5B, 5C:
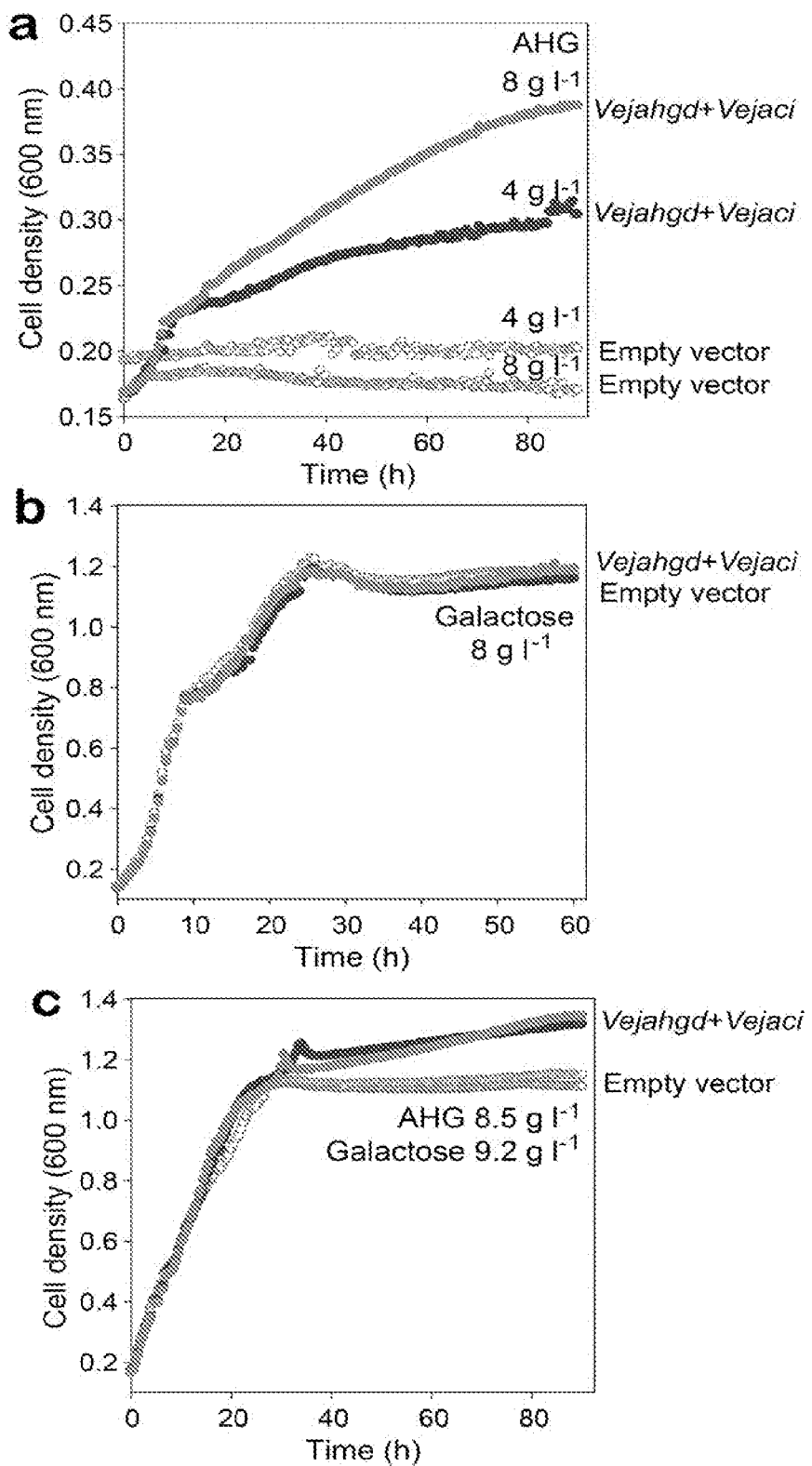
FIGS. 5a, 5b and 5c show a growth curve experiment result for recombinant microorganisms individually or simultaneously expressing 3,6-anhydro-L-galactose dehydrogenase and 3,6-anhydrogalactonic acid cycloisomerase according to the present invention under an aerobic condition using (FIG. 5a) 3,6-anhydro-L-galactose, (FIG. 5b) galactose or (FIG. 5c) an agarose hydrolysate containing 3,6-anhydro-L-galactose and galactose as a carbon source.

As a result, when the recombinant *E. coli* was cultured with an AHG as carbon source, it was confirmed that the *E. coli* was grown only under the condition of the recombination of the 3,6-anhydro-L-galactose dehydrogenase gene and the 3,6-anhydrogalactonic acid cycloisomerase gene (FIG. 5a). Also, under a galactose condition, the *E. coli* showed a similar growth curve to that under the condition of the addition of the empty vector and two enzyme genes (FIG. 5b), and under the condition in which an agarose hydrolysate predominantly containing AHG and galactose was used as carbon source, the growth curve was similar to other curves until 27 hour, and after that time, under the condition in which two enzyme genes were added, additional growth was shown (FIG. 5c).

Figure 6:
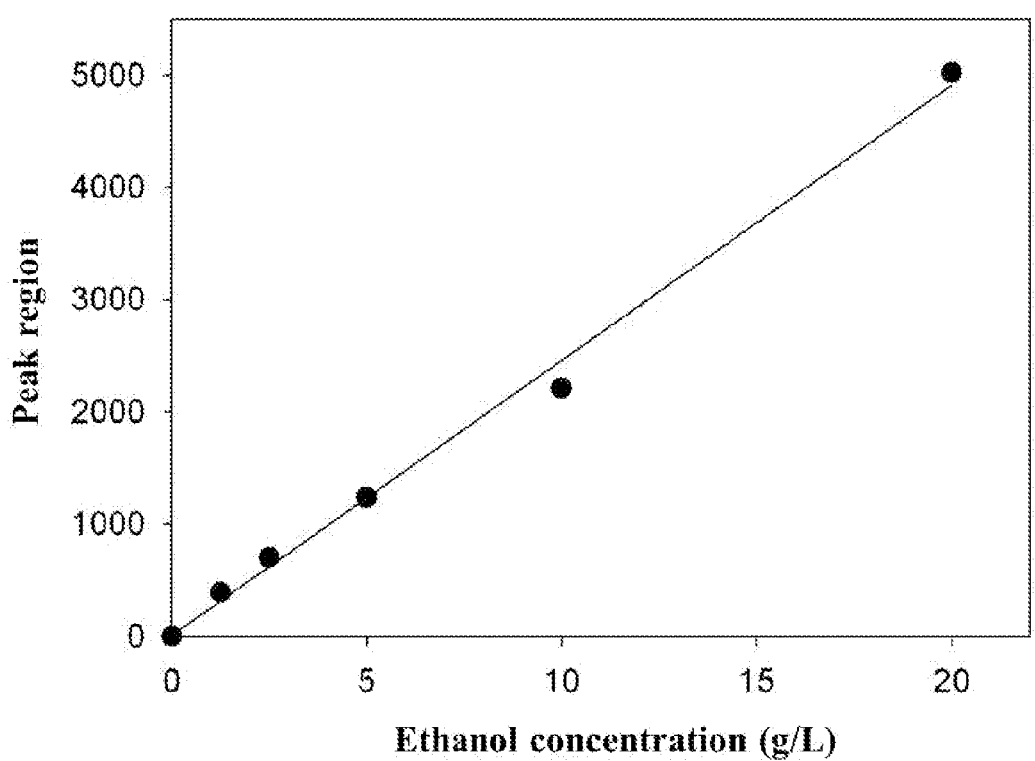
FIG. 6 shows a quantitative analysis curve of ethanol by GC-FID.

Also, the recombinant microorganism was subjected to an ethanol fermentation experiment under a microaerobic condition. Ethanol produced by fermenting the recombinant microorganism was analyzed by GC-FID depending on a concentration of an ethanol standard material to draw a calibration curve. A cell culture was centrifuged (16,000 rpm, 4° C., 5 minutes), a supernatant obtained thereby was analyzed, and analysis conditions are as follows: the inlet temperature: 250° C., the split ratio: 20:1, the pressure: 11.567 psi, the total flow: 24 mL/min, and the septum purge flow: 3 mL/min. 1 µl of a sample was injected. An oven flow was 1 mL/min, and an oven temperature was 40° C., maintained for 3.5 minutes, and elevated to 150° C. at a rate of 50° C/min, and a retention time of 1 minute was given. Afterward, the temperature was elevated to 180° C. at a rate of 20° C./min, a retention time was given for 2 minutes, and a total analysis time was 10.2 minutes. An FID temperature was 300° C., a hydrogen gas flow was 40 mL/min, an air flow was 350 mL/min, and a helium gas flow was 15 mL/min. According to the calibration curve of FIG. 6, the equation y=245.18x+12.24 (y=peak area, x=ethanol concentration (g/L)) was obtained, and based on this, the ethanol concentration was calculated.

Figures 7A, 7B, 7C:
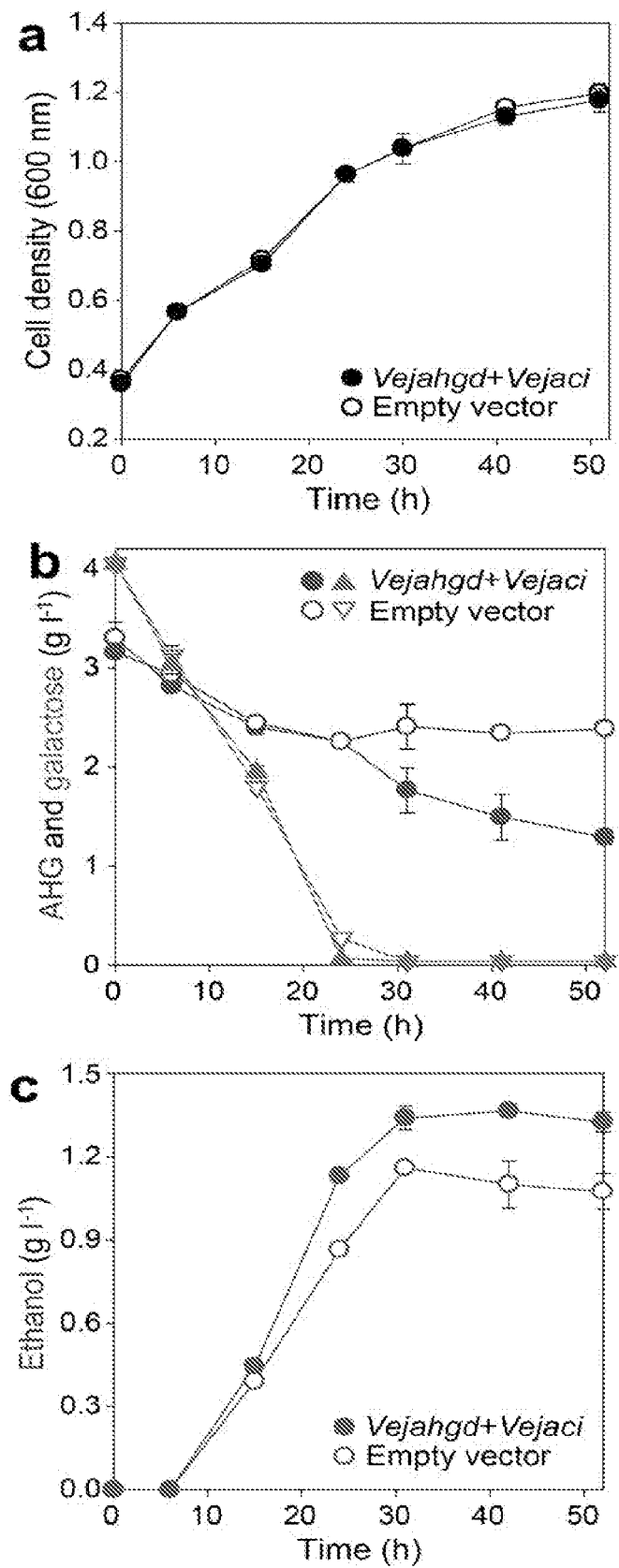
FIGS. 7a, 7b and 7c show (FIG. 7a) a growth curve experiment result for recombinant microorganisms individually or simultaneously expressing 3,6-anhydro-L-galactose dehydrogenase and 3,6-anhydrogalactonic acid cycloisomerase under fermentation conditions, (FIG. 7b) a result of measuring a substrate consumption ratio, and (FIG. 7c) a quantitative analysis result for ethanol produced by fermentation according to the present invention.

A cell density under the microaerobic condition was similar to that under the conditions of the empty vector and two enzyme genes (FIG. 7a), as the result of measuring a substrate consumption ratio, the consumption rate of galactose was similar, but beginning 24 hours after all galactose was consumed, AHG was consumed under the condition in which two enzyme genes were added (FIG. 7b). The ethanol was more highly produced under the condition in which two enzyme genes were added than the empty vector condition, and at 42 hours, compared to the empty vector condition, the ethanol concentration was 24% higher under the condition in which two enzyme genes were added.

EXAMPLE4

Production of Recombinant Microorganism for Expressing 3,6-AHG Metabolism-Associated Enzyme Family 3,6-AHG metabolism-associated enzyme family, that is, 3,6-anhydro-L-galactose dehydrogenase, 3,6-anhydrogalactonic acid cycloisomerase, 2-keto-3-deoxy-galactonic acid kinase, and 2-keto-3-deoxy-phosphogalactonic acid aldolase were introduced into *E. coli* KO11 FL strain for fermentation. Information on primers used herein is as follows:

1) 3,6-anhydro-L-galactose dehydrogenase-encoding gene (VEJY3_09240)

```
Forward primer 1:
(XhoI)
                                         (SEQ ID NO: 23)
5'-gcgctcgagatgaaacgttaccaaatgtacgttg-3'

Reverse primer 2:
(XbaI)
                                         (SEQ ID NO: 24)
5'-gcgtctagattagtcgaaattcacatagaatgtct-3'
```

2) 2-keto-3-deoxy-galactonic acid kinase-encoding gene+ 2-keto-3-deoxy-phosphogalactonic acid aldolase-encoding gene+3,6-anhydrogalactonic acid cycloisomerase-encoding gene (VEJY3_09380+VEJY3_09375+VEJY3_09370, respectively)

```
Forward primer 1:
(XbaI)
                                         (SEQ ID NO: 21)
5'-gcgtctagaatgagtttggaaataaaacaagatacg-3'

Reverse primer 2:
(SnabI)
                                         (SEQ ID NO: 22)
5'-gcgtacgta cacttcgtactgagcaattttgtc-3'
```

When the 3,6-anhydro-L-galactose dehydrogenase-encoding gene (ORF Names: VEJY3_09240) and the 2-keto-3-deoxy-galactonic acid kinase-encoding gene+2-keto-3-deoxy-phosphogalactonic acid aldolase-encoding gene+3,6-anhydrogalactonic acid cycloisomerase-encoding gene (VEJY3_09380+VEJY3_09375+VEJY3_09370, respectively) were simultaneously cloned into pBAD, an XbaI restriction site of VEJY3_09240 primer 2 and an XbaI restriction site of VEJY3_09380+VEJY3_09375+ VEJY3_09370 primer 1 were designed to be joined to each other by ligation, and XhoI and SnabI restriction sites at the ends of the VEJY3_09240 and VEJY3_09380+ VEJY3_09375+VEJY3_09370, which were joined to each other, were designed to be joined to the pBAD vector. Methods of enzyme expression and culture of the recombinant *E. coli* KO11 FL strain were the same as used for the recombinant *E. coli* K12 MG1655 produced in Examples 1 and 2. Here, as a carbon source for the medium, 1% galactose or 1% galactose+1% 3,6-AHG was used.

A growth experiment was carried out by culturing the recombinant microorganism. As a medium, the modified M9 medium described above was used, and the recombinant microorganism was cultured under a carbon source-free condition (control), a condition in which only 1% (w/v) 3,6-AHG was added without an inducing material, a condition in which only 0.01% (w/v) arabinose was present as an inducing material, and a condition in which 0.01% (w/v) arabinose was added to 1% (w/v) 3,6-AHG.

Figure 8:
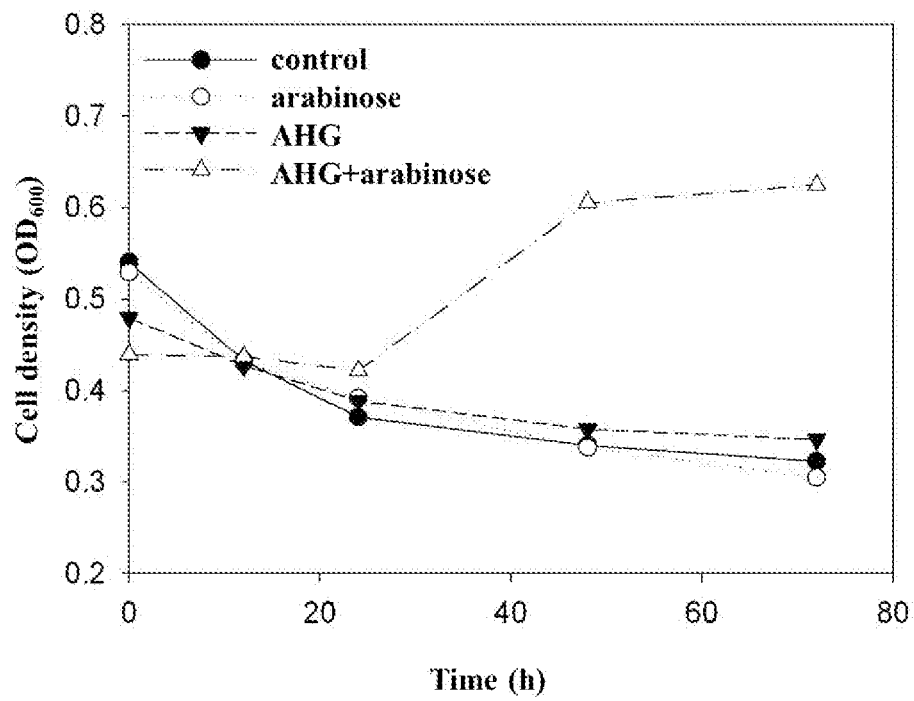
FIG. 8 shows a growth curve experiment result for recombinant microorganisms simultaneously expressing 3,6-anhydro-L-galactose dehydrogenase, 3,6-anhydrogalactonic acid cycloisomerase, 2-keto-3-deoxy-galactonic acid kinase, and 2-keto-3-deoxy-phosphogalactonic acid aldolase depending on a carbon source according to the present invention.

As shown in FIG. 8, only under the condition in which 0.01% (w/v) arabinose was added to 1%(w/v) 3,6-AHG an increase in cell density was observed.

The recombinant microorganism was fermented under the condition of a mixed sugar of an agarose degradation product, which is galactase, and 3,6-AHG. Here, fermentation was carried out under the conditions of 1% (w/v) galactose and the mixed sugar (1% (w/v) galactose+1% (w/v) 3,6-AHG), which were used as a carbon source of the medium, and 0.01% (w/v) arabinose was used as an inducing material.

Figure 9:
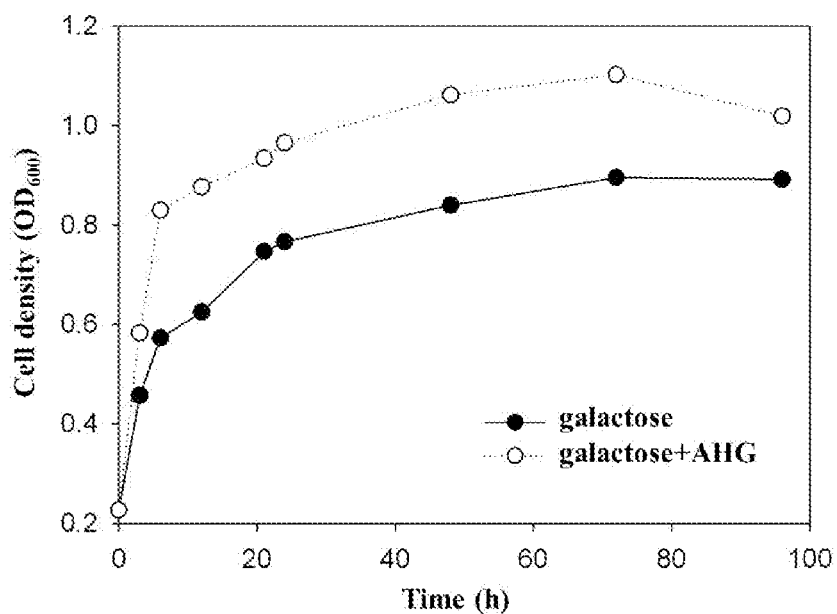
FIG. 9 shows a growth curve experiment result for recombinant microorganisms simultaneously expressing 3,6-anhydro-L-galactose dehydrogenase, 3,6-anhydrogalactonic acid cycloisomerase, 2-keto-3-deoxy-galactonic acid kinase and 2-keto-3-deoxy-phosphogalactonic acid aldolase under fermentation conditions according to the present invention.

As shown in FIG. 9, the cell density was higher under the mixed sugar condition than under the condition in which only 1% (w/v) galactose was added.

The recombinant microorganism was subjected to an alcohol fermentation experiment under a microaerobic condition by the same method as described in Example 3.

Figure 10:
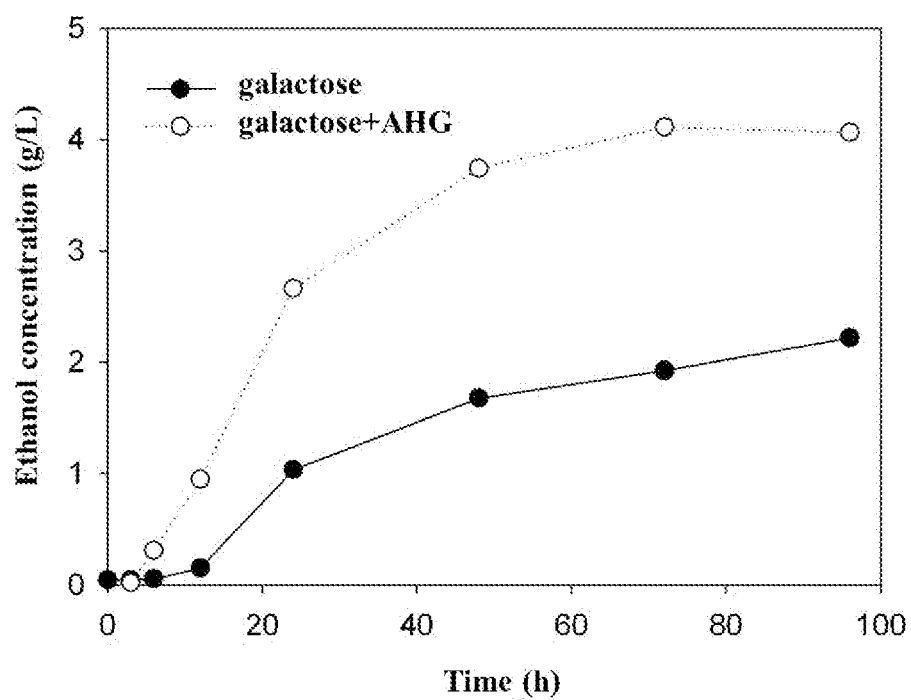
FIG. 10 shows a quantitative analysis result for ethanol produced by fermentation of recombinant microorganisms simultaneously expressing 3,6-anhydro-L-galactose dehydrogenase, 3,6-anhydrogalactonic acid cycloisomerase, 2-keto-3-deoxy-galactonic acid kinase and 2-keto-3-deoxy-phosphogalactonic acid aldolase according to the present invention.

As shown in FIG. 10, in the fermentation of the mixed sugar, 4.11 g/L of ethanol was produced, and in galactose fermentation, 1.93 g/L of ethanol was produced.

INDUSTRIAL AVAILABILITY

The present invention may be used in the field of producing bioethanol.

The invention claimed is:

1. A recombinant vector for producing ethanol, comprising:
   a polynucleotide encoding 3,6-anhydro-L-galactose dehydrogenase comprising the sequence of SEQ ID NO: 1;
   a polynucleotide encoding 3,6-anhydrogalactonic acid cycloisomerase comprising a sequence selected from the group consisting of: SEQ ID Nos: 3, 5 and 7;
   a polynucleotide encoding 2-keto-3-deoxy-galactonic acid kinase comprising the sequence of SEQ ID NO: 9; and
   a polynucleotide encoding 2-keto-3-deoxy-phosphogalactonic acid aldolase comprising the sequence of SEQ ID NO. 11.

2. A recombinant microorganism for producing ethanol, which is transformed by:
   a polynucleotide encoding 3,6-anhydro-L-galactose dehydrogenase comprising the sequence of SEQ ID NO: 1;
   a polynucleotide encoding 3,6-anhydrogalactonic acid cycloisomerase comprising a sequence selected from the group consisting of SEQ ID Nos: 3, 5 and 7;
   a polynucleotide encoding 2-keto-3-deoxy-galactonic acid kinase comprising the sequence of SEQ ID NO: 9; and
   a polynucleotide encoding 2-keto-3-deoxy-phosphogalactonic acid aldolase comprising the sequence of SEQ ID NO: 11.

3. The recombinant microorganism of claim 2, wherein the recombinant microorganism is transformed with:
   a recombinant vector comprising a polynucleotide encoding 3,6-anhydro-L-galactose dehydrogenase comprising the sequence of SE ID NO: 1;
   a recombinant vector comprising a polynucleotide encoding 3,6-anhydrogalactonic acid cycloisomerase comprising a sequence selected from the group consisting of: SEQ ID Nos: 3, 5 and 7;
   a recombinant vector comprising a polynucleotide encoding 2-keto-3-deoxy-galactonic acid kinase comprising the sequence of SEQ ID NO: 9; and
   a recombinant vector comprising a polynucleotide encoding 2-keto-3-deoxy-phosphogalactonic acid aldolase comprising the sequence of SEQ ID NO: 11.

4. The recombinant microorganism of claim 2, wherein the recombinant microorganism is transformed with:
   a recombinant vector comprising a polynucleotide encoding 3,6-anhydro-L-galactose dehydrogenase comprising the sequence of SEQ ID NO: 1 and a polynucleotide encoding 3,6-anhydrogalactonic acid cycloisomerase comprising a sequence selected from the group consisting of: SEQ ID Nos: 3, 5 and 7;
   a recombinant vector comprising a polynucleotide encoding 2-keto-3-deoxy-galactonic acid kinase comprising the sequence of SEQ ID NO: 9; and
   a recombinant vector comprising a polynucleotide encoding 2-keto-3-deoxy-phosphogalactonic acid aldolase comprising the sequence of SEQ ID NO: 11.

5. The recombinant microorganism of claim 2, wherein the recombinant microorganism is transformed with a recombinant vector comprising a polynucleotide encoding 3,6-anhydro-L-galactose dehydrogenase comprising the sequence of SEQ ID NO: 1, a polynucleotide encoding 3,6-anhydrogalactonic acid cycloisomerase comprising a sequence selected from the group consisting of: SEQ ID Nos: 3, 5 and 7, a polynucleotide encoding 2-keto-3-deoxy-galactonic acid kinase comprising the sequence of SEQ ID NO: 9 and a polynucleotide encoding 2-keto-3-deoxy-phosphogalactonic acid aldolase comprising the sequence of SEQ ID NO: 11.

6. The recombinant microorganism of claim 2, wherein the recombinant microorganism is selected from the group consisting of: *Escherichia coli, Bacillus subtilis, Streptomyces, Pseudomonas, Proteus mirabilis, Staphylococcus, Aspergillus, Pichia pastoris, Saccharomyces cerevisiae, Schizosaccharomyces* and *Neurospora crassa*.

7. A method of producing ethanol, comprising:
   fermenting the recombinant microorganism of claim 2 with one or more sugars selected from the group consisting of galactose and 3,6-anhydro-L-galactose as a carbon source.

8. The method of claim 7, wherein, arabinose is added as an inducing material on fermentation.

9. A method of producing ethanol, comprising:
   producing pyruvate by a reaction of a cell culture or cell extract of the recombinant microorganism of claim 2 with one or more substrates selected from the group consisting of galactose and 3,6-anhydro-L-galactose; and
   performing alcohol fermentation with the pyruvate.

* * * * *

SEQUENCE LISTING

```
<160> NUMBER OF SEQ ID NOS: 24

<210> SEQ ID NO 1
<211> LENGTH: 1443
<212> TYPE: DNA
<213> ORGANISM: Vibrio sp. EJY3
```

<400> SEQUENCE: 1

```
atgaaacgtt accaaatgta cgttgacggc cagtggattg acgctgagaa cggcaaagtt      60
gatcaggtta ttaacccgtc aaccgaagaa gtgcttgctg agattcagga tggtgaccaa     120
gatgatgctg agcgcgtttt aagtgtggct aaacgtgcac aatctgactg gaaacgagtg     180
cccgcgcgtc aacgtgctga actgttgaga agtttgctc aagaaatccg taataaccgt      240
gagcatcttg cagagttact cgtgagcgaa caaggcaaat tataccgagt tgcgttgggg     300
gaagtcgatg tagctgcatc ttttatcgaa tacgcctgtg actgggctcg tcagatggat     360
ggcgatattg ttcaatctga taatgtgaac aacatatct ggattcaaaa aattcctcgt      420
ggtgtcgtgg tcgcgatcac tgcatggaat ttcccatttg cattagcagg tcgcaagata     480
ggaccagcac tggttgcggg taacactatt gttgttaaac caacctctga aactccgcta     540
gcaacgctag agttaggcta tattgctgaa aaagtaggta ttcctgcagg tgtactcaat     600
atagttaccg gtggtggagc aagcttaggt ggcgctttaa ctagtcaccg ttatacaaat     660
atggtcacta tgacaggttc aacacccgtt ggtcagcaga taatcaaagc atctgcgaat     720
aacatggctc acgttcaact agagctcggt ggtaaagcac cgttcatcgt aatggaagat     780
gctgatctgg agcaagctgc tgccgctgca ctacattcac gcttcgacaa ctgtggtcag     840
gtatgtacat gtaacgaacg tatgtatgtg cactctagtg tctacgatga attcatggcg     900
atctttatgg agaaagtcca aaatatcaaa gtgggtaatc ctatggatcc agaatctgat     960
atgggtccta aagtaaacaa acgagagctt gatcatatgg aagcattagt cgcgcaggca    1020
ttgaaagaag gcgcgcaact tttgcatggt ggcaagcgcc ttacggaggg tgagtttgga    1080
aagggcttct ggtttgaacc cacaatctta ggtaatgttc aacaatcaat gacgattgtt    1140
catgaagagg catttggtcc aattcttcct gttataaaat tcgacacttt tgaagaagtc    1200
attgattacg caaatgatag tgagtatggc ttggcaacta tgatttgtac gcgaaatatg    1260
aagtatgtac atcgcttaac tcacgagctt gaatgtggtg agatttatgt gaaccgtggt    1320
catggagaac agcatcaagg tttccataat ggatataaac tgagcggaac tggtggtgaa    1380
gatggaaaat atggcttcga acaatattta gagaagaaga cattctatgt gaatttcgac    1440
taa                                                                  1443
```

<210> SEQ ID NO 2
<211> LENGTH: 480
<212> TYPE: PRT
<213> ORGANISM: Vibrio sp. EJY3

<400> SEQUENCE: 2

```
Met Lys Arg Tyr Gln Met Tyr Val Asp Gly Gln Trp Ile Asp Ala Glu
1               5                   10                  15

Asn Gly Lys Val Asp Gln Val Ile Asn Pro Ser Thr Glu Glu Val Leu
            20                  25                  30

Ala Glu Ile Gln Asp Gly Asp Gln Asp Ala Glu Arg Val Leu Ser
        35                  40                  45

Val Ala Lys Arg Ala Gln Ser Asp Trp Lys Arg Val Pro Ala Arg Gln
    50                  55                  60

Arg Ala Glu Leu Leu Arg Lys Phe Ala Gln Glu Ile Arg Asn Asn Arg
65                  70                  75                  80

Glu His Leu Ala Glu Leu Leu Val Ser Glu Gln Gly Lys Leu Tyr Arg
                85                  90                  95

Val Ala Leu Gly Glu Val Asp Val Ala Ala Ser Phe Ile Glu Tyr Ala
```

```
                    100                 105                 110
Cys Asp Trp Ala Arg Gln Met Asp Gly Asp Ile Val Gln Ser Asp Asn
            115                 120                 125

Val Asn Glu His Ile Trp Ile Gln Lys Ile Pro Arg Gly Val Val Val
    130                 135                 140

Ala Ile Thr Ala Trp Asn Phe Pro Phe Ala Leu Ala Gly Arg Lys Ile
145                 150                 155                 160

Gly Pro Ala Leu Val Ala Gly Asn Thr Ile Val Val Lys Pro Thr Ser
                165                 170                 175

Glu Thr Pro Leu Ala Thr Leu Glu Leu Gly Tyr Ile Ala Glu Lys Val
            180                 185                 190

Gly Ile Pro Ala Gly Val Leu Asn Ile Val Thr Gly Gly Gly Ala Ser
        195                 200                 205

Leu Gly Gly Ala Leu Thr Ser His Arg Tyr Thr Asn Met Val Thr Met
    210                 215                 220

Thr Gly Ser Thr Pro Val Gly Gln Gln Ile Ile Lys Ala Ser Ala Asn
225                 230                 235                 240

Asn Met Ala His Val Gln Leu Glu Leu Gly Gly Lys Ala Pro Phe Ile
                245                 250                 255

Val Met Glu Asp Ala Asp Leu Glu Gln Ala Ala Ala Ala Ala Leu His
            260                 265                 270

Ser Arg Phe Asp Asn Cys Gly Gln Val Cys Thr Cys Asn Glu Arg Met
        275                 280                 285

Tyr Val His Ser Ser Val Tyr Asp Glu Phe Met Ala Ile Phe Met Glu
    290                 295                 300

Lys Val Gln Asn Ile Lys Val Gly Asn Pro Met Asp Pro Glu Ser Asp
305                 310                 315                 320

Met Gly Pro Lys Val Asn Lys Arg Glu Leu Asp His Met Glu Ala Leu
                325                 330                 335

Val Ala Gln Ala Leu Lys Glu Gly Ala Gln Leu Leu His Gly Gly Lys
            340                 345                 350

Arg Leu Thr Glu Gly Glu Phe Gly Lys Gly Phe Trp Phe Glu Pro Thr
        355                 360                 365

Ile Leu Gly Asn Val Gln Gln Ser Met Thr Ile Val His Glu Glu Ala
    370                 375                 380

Phe Gly Pro Ile Leu Pro Val Ile Lys Phe Asp Thr Phe Glu Glu Val
385                 390                 395                 400

Ile Asp Tyr Ala Asn Asp Ser Glu Tyr Gly Leu Ala Thr Met Ile Cys
                405                 410                 415

Thr Arg Asn Met Lys Tyr Val His Arg Leu Thr His Glu Leu Glu Cys
            420                 425                 430

Gly Glu Ile Tyr Val Asn Arg Gly His Gly Glu Gln His Gln Gly Phe
        435                 440                 445

His Asn Gly Tyr Lys Leu Ser Gly Thr Gly Glu Asp Gly Lys Tyr
    450                 455                 460

Gly Phe Glu Gln Tyr Leu Glu Lys Lys Thr Phe Tyr Val Asn Phe Asp
465                 470                 475                 480

<210> SEQ ID NO 3
<211> LENGTH: 1152
<212> TYPE: DNA
<213> ORGANISM: Saccharophagus degradans 2-40

<400> SEQUENCE: 3
```

-continued

```
atgagtaaat gcctgatgga agtatagtg gaattagagt tgcctcaagg taacccaatt       60
aaaataaaat ccgtagcagt cgagcattac aaggttccgc tagctgaagt gttgtctgat     120
gcaaagcacg gggatcatac ctattttgag ctaatagtta gccgtatcac ttgccaaaat     180
ggtgtagaag gtgtgggtta tacctatacc ggtgggtccg gcggttcggc aatctattcg     240
ctattagtcg atgaaattaa gcctatgctt gttgggcggg acgccaccca aattctagcc     300
atatgggaag aaatttattg gcgcttacat tatgttgggc gcggtggttt agttagcttt     360
gctcagtcag cggttgatat tgcattgtgg gatattcgct gcaagttgtt ggggcaaccc     420
ctgtggaaag tggcgggcgg tttaagcaat aaaacacgct gctatgccgg cggtatagat     480
ttaaattttt cgcaagaaaa actattaagc aatatacaag gttatttaga cgcgggcttt     540
aatgctgtaa aaattaaagt tggcaaagat aatattaaag aagatattgc gcgtgtacgc     600
gcagtgcgag agttaattgg caaagatacc acatttatgg tggatgccaa ctactccatg     660
accaaagaaa aagccattcg ttttgctaac gccatagaag accaaaatat tacttggttt     720
gaagagccaa cattgccaga cgattaccaa ggctatgccg atatcgctca agcaatatca     780
ataccctag ctatgggtga aaacctacac actattcacg aatttaccta tgccgtgcaa     840
caagccaagc ttggtttttt gcagcccgat gcttctaata ttggtggtat tactggttgg     900
ttgaacgttg caagtttagc aaacgcacac aacttaccgg tgtgcagtca cggcatgcaa     960
gagttgcacg tttcacttat gtcgtctcag cccaatgcgg gttatttaga agttcactcc    1020
tttcctatcg accaatacac aacacaaccg ctagcaatgg aaaacggtta cgcactagca    1080
ccagatatag aaggcacggg tgttgtgttt gtcgatgaat tattacgtgg ccatttggct    1140
aaaaaaatcct aa                                                         1152
```

<210> SEQ ID NO 4
<211> LENGTH: 383
<212> TYPE: PRT
<213> ORGANISM: Saccharophagus degradans 2-40

<400> SEQUENCE: 4

```
Met Ser Lys Cys Leu Met Glu Ser Ile Val Glu Leu Glu Leu Pro Gln
1               5                   10                  15

Gly Asn Pro Ile Lys Ile Lys Ser Val Ala Val Glu His Tyr Lys Val
                20                  25                  30

Pro Leu Ala Glu Val Leu Ser Asp Ala Lys His Gly Asp His Thr Tyr
            35                  40                  45

Phe Glu Leu Ile Val Ser Arg Ile Thr Cys Gln Asn Gly Val Glu Gly
        50                  55                  60

Val Gly Tyr Thr Tyr Thr Gly Gly Ser Gly Gly Ser Ala Ile Tyr Ser
65                  70                  75                  80

Leu Leu Val Asp Glu Ile Lys Pro Met Leu Val Gly Arg Asp Ala Thr
                85                  90                  95

Gln Ile Leu Ala Ile Trp Glu Glu Ile Tyr Trp Arg Leu His Tyr Val
            100                 105                 110

Gly Arg Gly Gly Leu Val Ser Phe Ala Gln Ser Ala Val Asp Ile Ala
        115                 120                 125

Leu Trp Asp Ile Arg Cys Lys Leu Leu Gly Gln Pro Leu Trp Lys Val
    130                 135                 140

Ala Gly Gly Leu Ser Asn Lys Thr Arg Cys Tyr Ala Gly Gly Ile Asp
145                 150                 155                 160

Leu Asn Phe Ser Gln Glu Lys Leu Leu Ser Asn Ile Gln Gly Tyr Leu
```

```
                    165                 170                 175
Asp Ala Gly Phe Asn Ala Val Lys Ile Lys Val Gly Lys Asp Asn Ile
            180                 185                 190

Lys Glu Asp Ile Ala Arg Val Arg Ala Val Arg Glu Leu Ile Gly Lys
        195                 200                 205

Asp Thr Thr Phe Met Val Asp Ala Asn Tyr Ser Met Thr Lys Glu Lys
    210                 215                 220

Ala Ile Arg Phe Ala Asn Ala Ile Glu Asp Gln Asn Ile Thr Trp Phe
225                 230                 235                 240

Glu Glu Pro Thr Leu Pro Asp Asp Tyr Gln Gly Tyr Ala Asp Ile Ala
            245                 250                 255

Gln Ala Ile Ser Ile Pro Leu Ala Met Gly Glu Asn Leu His Thr Ile
        260                 265                 270

His Glu Phe Thr Tyr Ala Val Gln Gln Ala Lys Leu Gly Phe Leu Gln
    275                 280                 285

Pro Asp Ala Ser Asn Ile Gly Gly Ile Thr Gly Trp Leu Asn Val Ala
        290                 295                 300

Ser Leu Ala Asn Ala His Asn Leu Pro Val Cys Ser His Gly Met Gln
305                 310                 315                 320

Glu Leu His Val Ser Leu Met Ser Ser Gln Pro Asn Ala Gly Tyr Leu
            325                 330                 335

Glu Val His Ser Phe Pro Ile Asp Gln Tyr Thr Thr Gln Pro Leu Ala
        340                 345                 350

Met Glu Asn Gly Tyr Ala Leu Ala Pro Asp Ile Glu Gly Thr Gly Val
        355                 360                 365

Val Phe Val Asp Glu Leu Leu Arg Gly His Leu Ala Lys Lys Ser
    370                 375                 380

<210> SEQ ID NO 5
<211> LENGTH: 1137
<212> TYPE: DNA
<213> ORGANISM: Pseudoalteromonas atlantica T6c

<400> SEQUENCE: 5
atgagtgtca ttaccaaact agacacacct gccatgaaca gttcacaaat tcagtcagtc    60
aatgttgagt tattcaacgt gccccttgac gaagtgttga acgatgctaa gcacggcgat   120
catacccact ttgagctgat cctatgcacc attacttgta ccgatggtac tcaaggcgtg   180
ggttatacct acacaggtgg taaaggtgga cgcgctatat actcactgct taatgacgaa   240
ctaaagcctt tcttgatggg taaagatgct agctgcatca atcatttatg gaagaaatg   300 caatatcact tgcactatgt tggtcgtggc ggtttagtca gtttcgccat atccgcagtc   360
gatatcgccc tgtgggacat tcattgcaag gttcttaatc aacccttgtg gaaagtagct   420
gggggctgca gtgaccgcgt aaactgttat gcaggaggca ttgaccttaa tttttccact   480
gaaaaattgc tcggcaatat ccaaggctac ttagactgcg gctttgaagc ggtcaaaata   540
aaagtgggca agaagattac tcgtgaagac gtggcccgcg tggcggctgt gcgcaacctg   600
attggtcctg atgcgatatt tatggtggat gcaaattatt cacttacagt caataaagcc   660
attaagtttg ctcaggcgat agagcagtat gatatcaccct ggtttgaaga accgaccatt   720
cctgatgatt tgccggtttt tgctcacatt gccagcaaaa tcaatattcc gttggccatg   780
ggcgaaaacc tgcacactat ttacgaattc aaccaagcga taagccaagc caaacttggg   840
ttcttacaac ctgatgcatc gaatattggc ggtatcactg gttggctaac ggttgcccag   900
```

-continued

```
atgggctacg cgaacaactt acctatttgc agtcatggca tgcacgaatt acatgtatct    960
cttatggcat ctcagccaaa tgcgggttac ttggaagtac actcgtttcc cattgaccga   1020
tataccactc accctctgaa acttgaaaat ggcaaagccg ttgcgcccag tacacccggt   1080
gtaggcgtcg agttcaagac agagttactt cttccctatt tagttaaaca ttcttag     1137
```

<210> SEQ ID NO 6
<211> LENGTH: 378
<212> TYPE: PRT
<213> ORGANISM: Pseudoalteromonas atlantica T6c

<400> SEQUENCE: 6

```
Met Ser Val Ile Thr Lys Leu Asp Thr Pro Ala Met Asn Ser Ser Gln
1               5                   10                  15

Ile Gln Ser Val Asn Val Glu Leu Phe Asn Val Pro Leu Asp Glu Val
            20                  25                  30

Leu Asn Asp Ala Lys His Gly Asp His Thr His Phe Glu Leu Ile Leu
        35                  40                  45

Cys Thr Ile Thr Cys Thr Asp Gly Thr Gln Gly Val Gly Tyr Thr Tyr
    50                  55                  60

Thr Gly Gly Lys Gly Gly Arg Ala Ile Tyr Ser Leu Leu Asn Asp Glu
65                  70                  75                  80

Leu Lys Pro Phe Leu Met Gly Lys Asp Ala Ser Cys Ile Asn His Leu
                85                  90                  95

Trp Glu Glu Met Gln Tyr His Leu His Tyr Val Gly Arg Gly Gly Leu
            100                 105                 110

Val Ser Phe Ala Ile Ser Ala Val Asp Ile Ala Leu Trp Asp Ile His
        115                 120                 125

Cys Lys Val Leu Asn Gln Pro Leu Trp Lys Val Ala Gly Gly Cys Ser
    130                 135                 140

Asp Arg Val Asn Cys Tyr Ala Gly Gly Ile Asp Leu Asn Phe Ser Thr
145                 150                 155                 160

Glu Lys Leu Leu Gly Asn Ile Gln Gly Tyr Leu Asp Cys Gly Phe Glu
                165                 170                 175

Ala Val Lys Ile Lys Val Gly Lys Glu Asp Tyr Arg Glu Asp Val Ala
            180                 185                 190

Arg Val Ala Ala Val Arg Asn Leu Ile Gly Pro Asp Ala Ile Phe Met
        195                 200                 205

Val Asp Ala Asn Tyr Ser Leu Thr Val Asn Lys Ala Ile Lys Phe Ala
    210                 215                 220

Gln Ala Ile Glu Gln Tyr Asp Ile Thr Trp Phe Glu Glu Pro Thr Ile
225                 230                 235                 240

Pro Asp Asp Phe Ala Gly Phe Ala His Ile Ala Ser Lys Ile Asn Ile
                245                 250                 255

Pro Leu Ala Met Gly Glu Asn Leu His Thr Ile Tyr Glu Phe Asn Gln
            260                 265                 270

Ala Ile Ser Gln Ala Lys Leu Gly Phe Leu Gln Pro Asp Ala Ser Asn
        275                 280                 285

Ile Gly Gly Ile Thr Gly Trp Leu Thr Val Ala Gln Met Gly Tyr Ala
    290                 295                 300

Asn Asn Leu Pro Ile Cys Ser His Gly Met His Glu Leu His Val Ser
305                 310                 315                 320

Leu Met Ala Ser Gln Pro Asn Ala Gly Tyr Leu Glu Val His Ser Phe
                325                 330                 335
```

-continued

```
Pro Ile Asp Arg Tyr Thr Thr His Pro Leu Lys Leu Glu Asn Gly Lys
                340                 345                 350

Ala Val Ala Pro Ser Thr Pro Gly Val Gly Val Glu Phe Lys Thr Glu
            355                 360                 365

Leu Leu Leu Pro Tyr Leu Val Lys His Ser
        370                 375
```

<210> SEQ ID NO 7
<211> LENGTH: 1089
<212> TYPE: DNA
<213> ORGANISM: Vibrio sp. EJY3

<400> SEQUENCE: 7

```
atgaaaacaa caatcaaaga catcaaaacg agactgttta agattccgtt aaaggaaatt      60
ttatctgatg caaacatgg tgatcatgac cactttgagc tgatcactac aacggtcacg     120
ttagaagatg gttcgcaggg aaccggctat acttatactg gtggcaaagg cggttactcg     180
atcaaagcga tgctagagta tgatattcag cctgcgctaa tcggcaaaga cgcgacgcaa     240
attgaagaga tctatgactt tatggagtgg catattcact atgtcggtcg tggcggtatc     300
tctacatttg cgatgtctgc ggtagacatt gcgctttggg atctaaaagg taacgagaa      360
ggcttgccgt tatggaaaat ggctggtgga aaaaacaata cctgtaaagc gtactgtggt     420
ggcattgacc ttcagtttcc acttgagaaa ttgctcaaca atatttgtgg ttatttagaa     480
agtggcttca atgccgttaa gatcaagatt ggtcgcgaaa atatgcaaga agatattgac     540
cgcattaagg cggttcgcga gctgattggg ccagatatca cctttatgat cgatgccaac     600
tattcgttga cagtagaaca agcgatcaaa ctgtcaaaag cggtagagca aatgacatc      660
acgtggtttg aagagccaac attgccagat gactacaaag gttttgctga gattgctgac     720
aatacagcga ttccgttggc catggggaa aaccttcaca ccattcatga gtttggttat      780
gcaatggacc aagcaaagct tggctactgc caaccagatg cctcaaactg tggtggcatt     840
accggttggt tgaaagcggc ggacttgatt acagaacata atatcccagt gtgtactcac     900
ggtatgcaag agctacacgt aagtcttgtt tcagcgtttg atacaggttg gctagaggtg     960
cacagcttcc cgattgatga atacaccaag cgtcctttgg ttgtagaaaa cttccgcgct    1020
gtggcgtcca atgagccggg tatcggggtc gagttcgatt gggacaaaat gctcagtac    1080
gaagtgtaa                                                            1089
```

<210> SEQ ID NO 8
<211> LENGTH: 362
<212> TYPE: PRT
<213> ORGANISM: Vibrio sp. EJY3

<400> SEQUENCE: 8

```
Met Lys Thr Thr Ile Lys Asp Ile Lys Thr Arg Leu Phe Lys Ile Pro
  1               5                  10                  15

Leu Lys Glu Ile Leu Ser Asp Ala Lys His Gly Asp His Asp His Phe
                20                  25                  30

Glu Leu Ile Thr Thr Thr Val Thr Leu Glu Asp Gly Ser Gln Gly Thr
            35                  40                  45

Gly Tyr Thr Tyr Thr Gly Gly Lys Gly Gly Tyr Ser Ile Lys Ala Met
        50                  55                  60

Leu Glu Tyr Asp Ile Gln Pro Ala Leu Ile Gly Lys Asp Ala Thr Gln
 65                  70                  75                  80

Ile Glu Glu Ile Tyr Asp Phe Met Glu Trp His Ile His Tyr Val Gly
```

```
            85                  90                  95
Arg Gly Gly Ile Ser Thr Phe Ala Met Ser Ala Val Asp Ile Ala Leu
            100                 105                 110

Trp Asp Leu Lys Gly Lys Arg Glu Gly Leu Pro Leu Trp Lys Met Ala
            115                 120                 125

Gly Gly Lys Asn Asn Thr Cys Lys Ala Tyr Cys Gly Ile Asp Leu
130                 135                 140

Gln Phe Pro Leu Glu Lys Leu Leu Asn Asn Ile Cys Gly Tyr Leu Glu
145                 150                 155                 160

Ser Gly Phe Asn Ala Val Lys Ile Lys Ile Gly Arg Glu Asn Met Gln
                165                 170                 175

Glu Asp Ile Asp Arg Ile Lys Ala Val Arg Glu Leu Ile Gly Pro Asp
            180                 185                 190

Ile Thr Phe Met Ile Asp Ala Asn Tyr Ser Leu Thr Val Glu Gln Ala
            195                 200                 205

Ile Lys Leu Ser Lys Ala Val Glu Gln Tyr Asp Ile Thr Trp Phe Glu
210                 215                 220

Glu Pro Thr Leu Pro Asp Asp Tyr Lys Gly Phe Ala Glu Ile Ala Asp
225                 230                 235                 240

Asn Thr Ala Ile Pro Leu Ala Met Gly Glu Asn Leu His Thr Ile His
                245                 250                 255

Glu Phe Gly Tyr Ala Met Asp Gln Ala Lys Leu Gly Tyr Cys Gln Pro
            260                 265                 270

Asp Ala Ser Asn Cys Gly Gly Ile Thr Gly Trp Leu Lys Ala Ala Asp
            275                 280                 285

Leu Ile Thr Glu His Asn Ile Pro Val Cys Thr His Gly Met Gln Glu
290                 295                 300

Leu His Val Ser Leu Val Ser Ala Phe Asp Thr Gly Trp Leu Glu Val
305                 310                 315                 320

His Ser Phe Pro Ile Asp Glu Tyr Thr Lys Arg Pro Leu Val Val Glu
                325                 330                 335

Asn Phe Arg Ala Val Ala Ser Asn Glu Pro Gly Ile Gly Val Glu Phe
            340                 345                 350

Asp Trp Asp Lys Ile Ala Gln Tyr Glu Val
            355                 360

<210> SEQ ID NO 9
<211> LENGTH: 966
<212> TYPE: DNA
<213> ORGANISM: Vibrio sp. EJY3

<400> SEQUENCE: 9
atgagtttgg aaataaaaca agatacggag tctagctata gcgatattct tagctttggt      60
gagccaatgt ttgagtttag ccaagttgga caagcaggtt caggccagcc tgatttcttg     120
agtggttttg gtggtgatgc ttcgaacttt gctatcgcag cagcaagaca aggcgcatca     180
gttggaatgt tgacacaact tggcgacgat gaattcggta agcgttttgt tgagctgtgg     240
gaacagcagg gtgttagcag ttcagctgtg tgtatactac caaataaagc aacgggcgtt     300
tattttatta cgcacgatga tgagggacac cattttttct tcttgcgtaa gaactctgcg     360
gccagtttaa tgacaccgca agacttacca tcagatgcga ttgccaatgc taagcttctt     420
catatcactg ctattactca ggcgattagt gattcaagtt gtgactcagt gtttgcagca     480
attgaaacag cgaaagcgca cggcactcaa gtgtcctatg acaccaactt gcgcttaaag     540
```

| | | | | |
|---|---|---|---|---|
| ctatggtcac tgcaacgcgc tcgcgccatc attaatgaaa ccgcgtcact agtcgatgtc | | | | 600 |
| tgcttcccta gtattgacga agcacgcttg gtgactggcc ttgaacatgc tgacgatatc | | | | 660 |
| atcgattttt acctaaaagc aggcgcgaaa gttgtcgtac ttaaacaggg tggtgacggt | | | | 720 |
| gcgacagtgg ctaatgagca tattaggcat ttcatccttc cgcataaagt gacacctgtt | | | | 780 |
| gatgcgaccg ctgctggtga ttcatttgca ggctcattct gtacgcatta tgtcaacgga | | | | 840 |
| gagtctttag agcagtgtct tgcgtatgca aatgccaccg cgtctatcac gattactggt | | | | 900 |
| tttggtgcag ttgccccttt accgacattt gagcaagtgc ttgagaaaat caacgaatct | | | | 960 |
| aaatag | | | | 966 |

<210> SEQ ID NO 10
<211> LENGTH: 321
<212> TYPE: PRT
<213> ORGANISM: Vibrio sp. EJY3

<400> SEQUENCE: 10

```
Met Ser Leu Glu Ile Lys Gln Asp Thr Glu Ser Ser Tyr Ser Asp Ile
1               5                   10                  15

Leu Ser Phe Gly Glu Pro Met Phe Glu Phe Ser Gln Val Gly Gln Ala
            20                  25                  30

Gly Ser Gly Gln Pro Asp Phe Leu Ser Gly Phe Gly Gly Asp Ala Ser
        35                  40                  45

Asn Phe Ala Ile Ala Ala Ala Arg Gln Gly Ala Ser Val Gly Met Leu
    50                  55                  60

Thr Gln Leu Gly Asp Asp Glu Phe Gly Lys Arg Phe Val Glu Leu Trp
65                  70                  75                  80

Glu Gln Gln Gly Val Ser Ser Ser Ala Val Cys Ile Leu Pro Asn Lys
                85                  90                  95

Ala Thr Gly Val Tyr Phe Ile Thr His Asp Asp Glu Gly His His Phe
            100                 105                 110

Ser Phe Leu Arg Lys Asn Ser Ala Ala Ser Leu Met Thr Pro Gln Asp
        115                 120                 125

Leu Pro Ser Asp Ala Ile Ala Asn Ala Lys Leu Leu His Ile Thr Ala
    130                 135                 140

Ile Thr Gln Ala Ile Ser Asp Ser Ser Cys Asp Ser Val Phe Ala Ala
145                 150                 155                 160

Ile Glu Thr Ala Lys Ala His Gly Thr Gln Val Ser Tyr Asp Thr Asn
                165                 170                 175

Leu Arg Leu Lys Leu Trp Ser Leu Gln Arg Ala Arg Ala Ile Ile Asn
            180                 185                 190

Glu Thr Ala Ser Leu Val Asp Val Cys Phe Pro Ser Ile Asp Glu Ala
        195                 200                 205

Arg Leu Val Thr Gly Leu Glu His Ala Asp Asp Ile Ile Asp Phe Tyr
    210                 215                 220

Leu Lys Ala Gly Ala Lys Val Val Leu Lys Gln Gly Gly Asp Gly
225                 230                 235                 240

Ala Thr Val Ala Asn Glu His Ile Arg His Phe Ile Leu Pro His Lys
                245                 250                 255

Val Thr Pro Val Asp Ala Thr Ala Gly Asp Ser Phe Ala Gly Ser
            260                 265                 270

Phe Cys Thr His Tyr Val Asn Gly Glu Ser Leu Glu Gln Cys Leu Ala
        275                 280                 285

Tyr Ala Asn Ala Thr Ala Ser Ile Thr Ile Thr Gly Phe Gly Ala Val
```

```
                290              295              300
Ala Pro Leu Pro Thr Phe Glu Gln Val Leu Glu Lys Ile Asn Glu Ser
305                 310              315              320

Lys

<210> SEQ ID NO 11
<211> LENGTH: 621
<212> TYPE: DNA
<213> ORGANISM: Vibrio sp. EJY3

<400> SEQUENCE: 11
atggatctca atcaacgttt agctaagctc aaagttgtgc ctgtgattgc tgtagataat      60
gcgcaagata ttttgccttt aggtaaggcg ctggtagaga atggtttacc agtcgcagaa     120
attacccttc gctctgacgc ggcgactgaa gccattcgtt acttcgtac tacttatcca      180 gacatcttga ttggtgcggg tacggtattg aacgaagctc aagtaattga ggcaaaagag     240
gcgggtgctg actttattgt ttctccaggc ttgaacccaa tcacagtaaa agcatgtcaa     300
aaacataaaa taaccatcgt ccctggtgta acagcccat cgttggttga gcaagctctt      360
gagcttggtg ttgatactgt taaattttc ccagcagaag cgtcgggcgg tctagcgatg      420
ttgaagtcgt tgcttggccc ttatcaacaa atcaaagtga tgcctacagg tggtatcaat     480
caaaacaaca ttcatgatta tctggctctt cctgctgtac ttgcttgtgg tggtacgtgg     540
atggtggata atcactggt acataaaggt gcttgggatg aaattggccg attggtcaga      600
gaaattgtcg ccgcagtata g                                                621

<210> SEQ ID NO 12
<211> LENGTH: 206
<212> TYPE: PRT
<213> ORGANISM: Vibrio sp. EJY3

<400> SEQUENCE: 12

Met Asp Leu Asn Gln Arg Leu Ala Lys Leu Lys Val Val Pro Val Ile
1               5                   10                  15

Ala Val Asp Asn Ala Gln Asp Ile Leu Pro Leu Gly Lys Ala Leu Val
                20                  25                  30

Glu Asn Gly Leu Pro Val Ala Glu Ile Thr Phe Arg Ser Asp Ala Ala
            35                  40                  45

Thr Glu Ala Ile Arg Leu Leu Arg Thr Thr Tyr Pro Asp Ile Leu Ile
        50                  55                  60

Gly Ala Gly Thr Val Leu Asn Glu Ala Gln Val Ile Glu Ala Lys Glu
65                  70                  75                  80

Ala Gly Ala Asp Phe Ile Val Ser Pro Gly Leu Asn Pro Ile Thr Val
                85                  90                  95

Lys Ala Cys Gln Lys His Lys Ile Thr Ile Val Pro Gly Val Asn Ser
                100                 105                 110

Pro Ser Leu Val Glu Gln Ala Leu Glu Leu Gly Val Asp Thr Val Lys
            115                 120                 125

Phe Phe Pro Ala Glu Ala Ser Gly Gly Leu Ala Met Leu Lys Ser Leu
        130                 135                 140

Leu Gly Pro Tyr Gln Gln Ile Lys Val Met Pro Thr Gly Gly Ile Asn
145                 150                 155                 160

Gln Asn Asn Ile His Asp Tyr Leu Ala Leu Pro Ala Val Leu Ala Cys
                165                 170                 175

Gly Gly Thr Trp Met Val Asp Lys Ser Leu Val His Lys Gly Ala Trp
```

```
                180               185               190
Asp Glu Ile Gly Arg Leu Val Arg Glu Ile Val Ala Ala Val
        195               200               205

<210> SEQ ID NO 13
<211> LENGTH: 40
<212> TYPE: DNA
<213> ORGANISM: Artificial Sequence
<220> FEATURE:
<223> OTHER INFORMATION: Forward primer 1 for 3,6-anhydro-L-galactose
      dehydrogenase

<400> SEQUENCE: 13
gaaggagata taaggatgaa acgttaccaa atgtacgttg                       40

<210> SEQ ID NO 14
<211> LENGTH: 40
<212> TYPE: DNA
<213> ORGANISM: Artificial Sequence
<220> FEATURE:
<223> OTHER INFORMATION: Reverse primer 2 for 3,6-anhydro-L-galactose
      dehydrogenase

<400> SEQUENCE: 14
atgatggtga tggtggtcga aattcacata gaatgtcttc                       40

<210> SEQ ID NO 15
<211> LENGTH: 47
<212> TYPE: DNA
<213> ORGANISM: Artificial Sequence
<220> FEATURE:
<223> OTHER INFORMATION: Forward primer 1 for SdeACI

<400> SEQUENCE: 15
gaaggagata taaggatgaa aattcataac atgaaaaatt ttatcaa               47

<210> SEQ ID NO 16
<211> LENGTH: 40
<212> TYPE: DNA
<213> ORGANISM: Artificial Sequence
<220> FEATURE:
<223> OTHER INFORMATION: Reverse primer 2 for SdeACI

<400> SEQUENCE: 16
atgatggtga tggtgtcatt cagcaaaata cactgtcttc                       40

<210> SEQ ID NO 17
<211> LENGTH: 43
<212> TYPE: DNA
<213> ORGANISM: Artificial sequence
<220> FEATURE:
<223> OTHER INFORMATION: Forward primer 1 for Pat1ACI

<400> SEQUENCE: 17
gaaggagata taaggatgat gagtgtcatt accaaactag aca                   43

<210> SEQ ID NO 18
<211> LENGTH: 42
<212> TYPE: DNA
<213> ORGANISM: Artificial Sequence
<220> FEATURE:
<223> OTHER INFORMATION: Reverse primer 2 for Pat1ACI

<400> SEQUENCE: 18
atgatggtga tggtgagaat gtttaactaa atagggaaga ag                    42
```

```
<210> SEQ ID NO 19
<211> LENGTH: 43
<212> TYPE: DNA
<213> ORGANISM: Artificial Sequence
<220> FEATURE:
<223> OTHER INFORMATION: Forward primer 1 for Vejy3ACI

<400> SEQUENCE: 19
gaaggagata taaggatgaa acaacaatc aaagacatca aaa                43

<210> SEQ ID NO 20
<211> LENGTH: 38
<212> TYPE: DNA
<213> ORGANISM: Artificial Sequence
<220> FEATURE:
<223> OTHER INFORMATION: Reverse primer 2 for Vejy3ACI

<400> SEQUENCE: 20
atgatggtga tggtgcactt cgtactgagc aattttgt                     38

<210> SEQ ID NO 21
<211> LENGTH: 38
<212> TYPE: DNA
<213> ORGANISM: Artificial Sequence
<220> FEATURE:
<223> OTHER INFORMATION: Forward primer 1 for Vejy3ACI

<400> SEQUENCE: 21
gcgctcgaga tgaaaacaac aatcaaagac atcaaaac                     38

<210> SEQ ID NO 22
<211> LENGTH: 33
<212> TYPE: DNA
<213> ORGANISM: Artificial Sequence
<220> FEATURE:
<223> OTHER INFORMATION: Reverse primer 2 for Vejy3ACI

<400> SEQUENCE: 22
gcgtacgtac acttcgtact gagcaattttt gtc                         33

<210> SEQ ID NO 23
<211> LENGTH: 34
<212> TYPE: DNA
<213> ORGANISM: Artificial Sequence
<220> FEATURE:
<223> OTHER INFORMATION: Forward primer 1 for 3,6-anhydro-L-galactose
      dehydrogenase

<400> SEQUENCE: 23
gcgctcgaga tgaaacgtta ccaaatgtac gttg                         34

<210> SEQ ID NO 24
<211> LENGTH: 35
<212> TYPE: DNA
<213> ORGANISM: Artificial Sequence
<220> FEATURE:
<223> OTHER INFORMATION: Reverse primer 2 for 3,6-anhydro-L-galactose
      dehydrogenase

<400> SEQUENCE: 24
gcgtctagat tagtcgaaat tcacatagaa tgtct                        35
```